(12) United States Patent
Kim et al.

(10) Patent No.: US 8,317,716 B2
(45) Date of Patent: Nov. 27, 2012

(54) DIAGNOSIS SYSTEM OF DEFICIENT AND FORCEFUL PULSE

(75) Inventors: Jong Yeol Kim, Daejeon (KR); Jeon Lee, Daejeon (KR); Yu Jung Lee, Daejeon (KR); Si Woo Lee, Daejeon (KR); Jaehwan Kang, Daejeon (KR); Hyunhee Ryu, Ansan-si (KR); Hae-Jung Lee, Daejeon (KR); Eun-Ji Choi, Yongin-si (KR)

(73) Assignee: Korea Institute of Oriental Medicine, Daejeon (KR)

( * ) Notice: Subject to any disclaimer, the term of this patent is extended or adjusted under 35 U.S.C. 154(b) by 573 days.

(21) Appl. No.: 12/531,246

(22) PCT Filed: Sep. 28, 2007

(86) PCT No.: PCT/KR2007/004748
§ 371 (c)(1),
(2), (4) Date: Sep. 14, 2009

(87) PCT Pub. No.: WO2008/111713
PCT Pub. Date: Sep. 18, 2008

(65) Prior Publication Data
US 2010/0022895 A1 Jan. 28, 2010

(30) Foreign Application Priority Data
Mar. 14, 2007 (KR) .................. 10-2007-0025023

(51) Int. Cl.
*A61B 5/02* (2006.01)
(52) U.S. Cl. ...................................... 600/500; 600/503

(58) Field of Classification Search ........... 600/500–503
See application file for complete search history.

(56) References Cited

U.S. PATENT DOCUMENTS

| | | | |
|---|---|---|---|
| 4,561,447 A | 12/1985 | Kawamura et al. | |
| 5,396,895 A | 3/1995 | Takashima et al. | |
| 5,733,096 A * | 3/1998 | Van Doren et al. | 414/744.3 |
| 6,210,340 B1 * | 4/2001 | Amano et al. | 600/500 |
| 6,261,235 B1 * | 7/2001 | Amano et al. | 600/485 |
| 2002/0065471 A1 | 5/2002 | Amano et al. | |
| 2003/0212335 A1 * | 11/2003 | Huang | 600/500 |

FOREIGN PATENT DOCUMENTS

| | | |
|---|---|---|
| KR | 1019960007548 B1 | 6/1996 |
| KR | 100158047 B1 | 8/1998 |
| KR | 200261625 B1 | 1/2002 |
| KR | 1020020009068 A | 2/2002 |

* cited by examiner

*Primary Examiner* — Michael Kahelin
*Assistant Examiner* — Tho Tran
(74) *Attorney, Agent, or Firm* — Lucas & Mercanti, LLP

(57) ABSTRACT

Disclosed herein is a system for diagnosing a deficient pulse and an forceful pulse. The system includes a pulse diagnostic device, a deficient pulse and forceful pulse determining device, and an output device. The pulse diagnostic device measures pulse condition information at an examinee's Cun (~\f~) Gu (H), and Chi (,R) pulse-taking locations on his or her wrist using one or more pulse-taking sensors. The deficient pulse and forceful pulse determining device is operably connected to the pulse diagnostic device, analyzes the pulse pressure information measured by the pulse diagnostic device, calculates a quantified deficiency/forceful coefficient, and determines whether a pulse of interest is a deficient pulse or an forceful pulse. The output device is connected to the determining device and displays results of the determination.

14 Claims, 19 Drawing Sheets

* Cun, Gu, and Chi pulse-taking locations

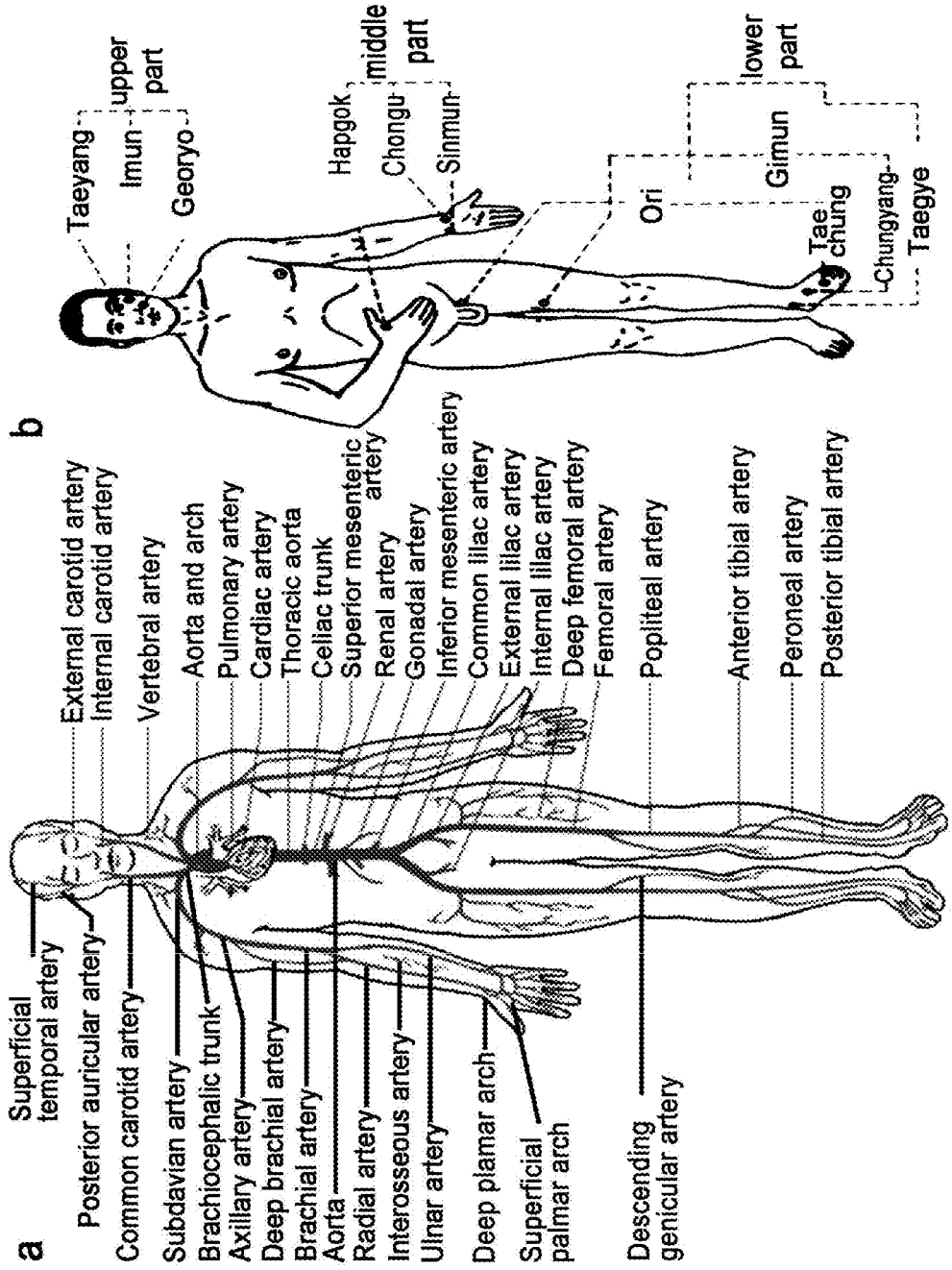

Fig. 3 Cun, Gu, and Chi pulse-taking locations
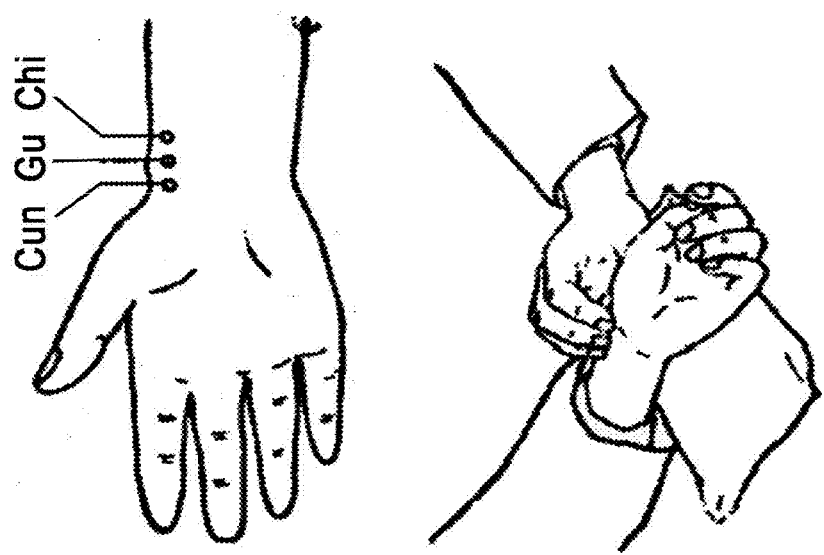

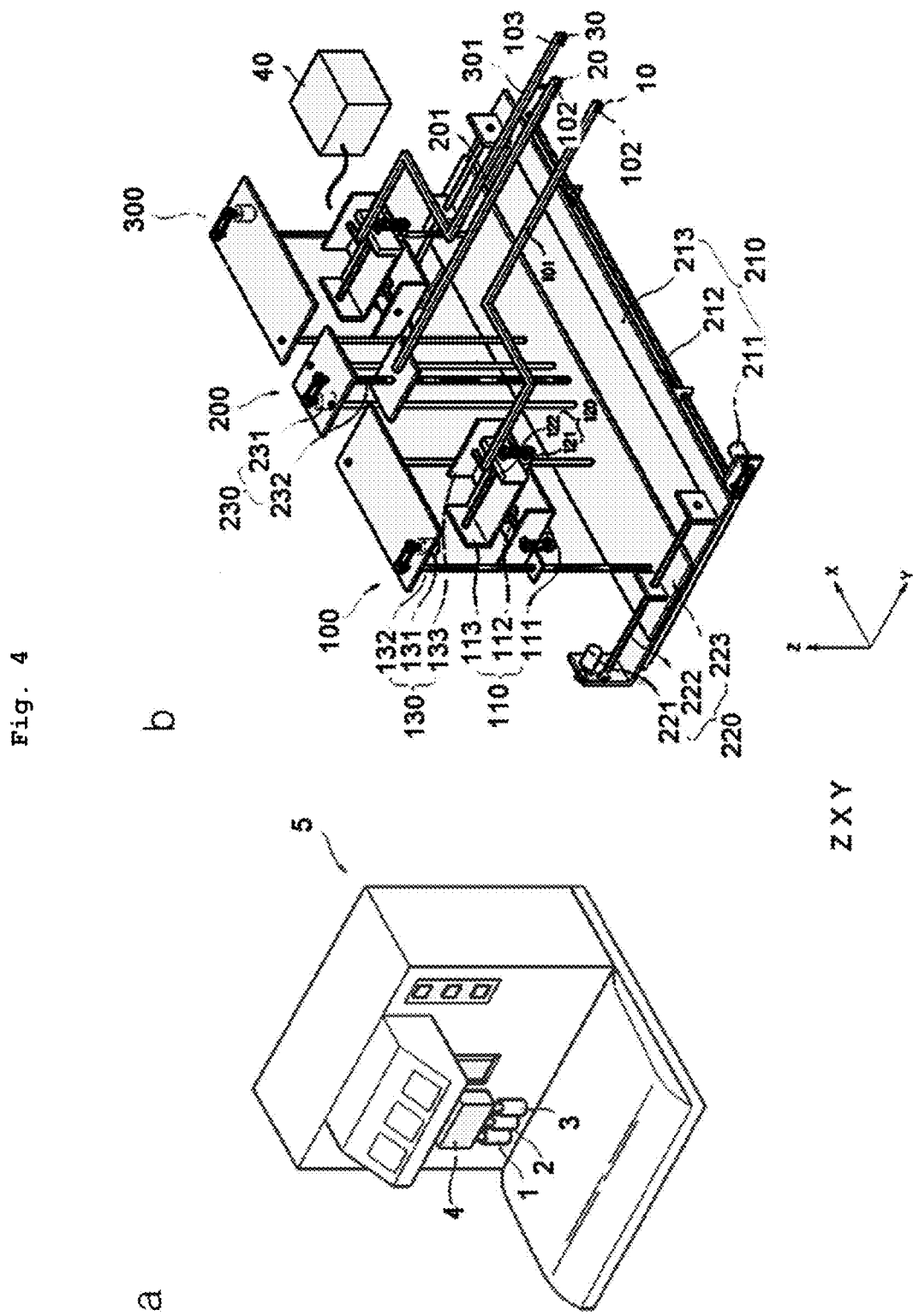

Fig. 6
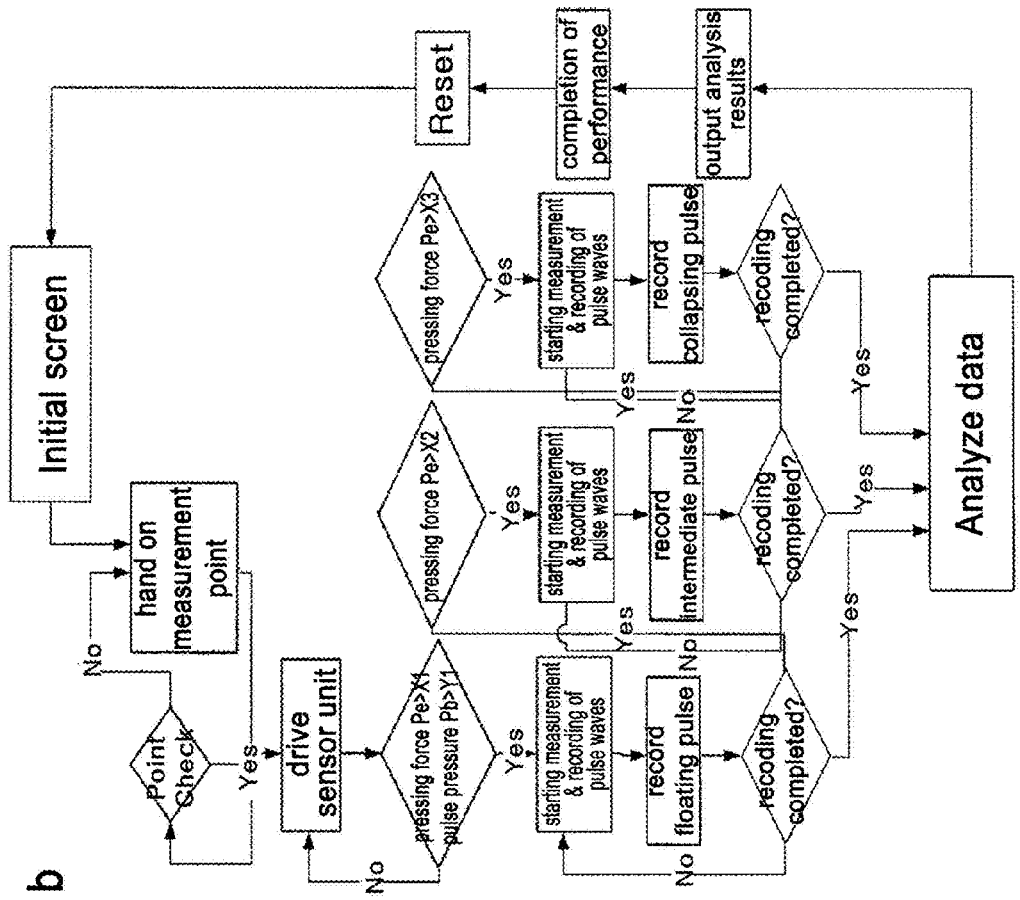
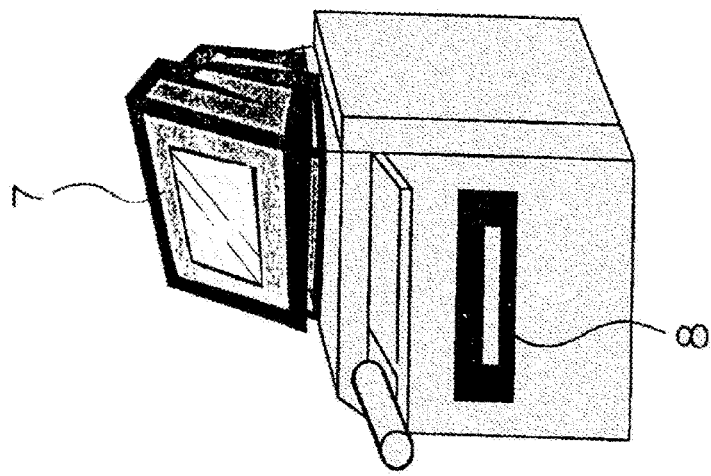

DIAGNOSIS SYSTEM OF DEFICIENT AND FORCEFUL PULSE

CROSS-REFERENCE TO RELATED APPLICATIONS

This application is a 371 of PCT/KR2007/004748 filed on Sep. 28, 2007, which claims the benefit of Korean Patent Application No. 10-2007-0025023 filed on Mar. 14, 2007, the contents of each of which are incorporated herein by reference.

TECHNICAL FIELD

The present invention relates, in general, to a system for diagnosing a deficient pulse and an forceful pulse, and, more particularly, to a system for diagnosing a deficient pulse and an forceful pulse, including a pulse diagnostic device configured to measure pulse condition information at an examinee's Cun (寸), Gu (關), and Chi (尺) pulse-taking locations on his or her wrist using one or more pulse-taking sensors, a deficient pulse and forceful pulse determining device operably connected to the pulse diagnostic device and configured to analyze the pulse pressure information measured by the pulse diagnostic device, to calculate a quantified deficiency/forceful coefficient and to determine whether the pulse of interest is a deficient pulse or an forceful pulse, and an output device connected to the determining device and configured to display the results of the determination.

BACKGROUND ART

Generally, the diagnostic techniques of traditional Oriental medicine mainly include four diagnostic methods, namely, auscultation, olfaction, inspection, and palpation. Pulse diagnosis, which is one of the diagnosis methods of traditional oriental medicine, falls under palpation. The tactile sensation of pulse, obtained through the tips of the fingers, is described in terms of pulse conditions (脈象), and the pulse conditions, determined through the various tactile sensations through the tips of the fingers, are used for diagnosis. A human's finger includes hundreds of thousands of sensory cells, and the sensation of each finger varies with the individual according to the extent of development. Consequently, pulse conditions that have been used since the age when there were no measuring instruments have been handed down orally and have been instructed through experience, and thus have obscure termination criteria and are difficult to standardize (refer to FIG. 1).

In traditional oriental medicine, various types of pulse diagnoses have been used to detect pulse conditions. In the currently used "Three sector pulse-taking method (三部脈法)," pulsation is measured in the state in which an examiner's three fingers, that is, his or her middle finger and the two fingers flanking the middle finger, are placed on the Cun, Gu, and Chi pulse-taking locations on the inside of the left wrist.

FIG. 2 shows the anatomical arterial circulatory system and pulse-taking locations in traditional oriental medicine. From FIG. 3, it can be seen that the Cun, Gu and Chi pulse-taking locations are present on the radius artery of the left wrist.

At the time of pulse taking, an examiner places his or her middle finger on the Gu pulse-taking location, that is, the location of the radius artery on the eminent head of the radius, places his or her index finger and third finger on the Cun pulse-taking location spaced apart from the Gu pulse-taking location toward the palm by 10~13 mm, and the Chi pulse-taking location spaced apart from the Gu pulse-taking location toward his or her elbow by 10~13 mm, and then measures pulsation sensed by the three fingers. In this state, the examiner diagnoses the condition of pulsation while pressing the three fingers. In the first step, the examiner searches for the pressing range within which pulsation is sensed while increasing and decreasing pressing force. At the subsequent step, the examiner searches for the maximum pulse pressure while gradually increasing the pressing force. The pulse pressure at which the maximum force of a pulse is sensed is referred to as the 'maximum pulse pressure'. In brief, when an examiner diagnoses the state of a disease using a pulse diagnotic method, the examiner places three fingers at the three Cun, Gu and Chi pulse-taking locations, senses a pulse condition at the maximum pulse pressure within the pressing range within which pulsation is sensed while varying the pressing force, and makes a diagnosis.

However, when a human directly performs pulse diagnosis, an examinee's pulse condition is determined depending entirely on the examiner's subjective senses and experiences, so that diagnosis results may vary with the examiner and the reliability of diagnosis may be reduced.

Research into a pulse wave measurement device that is capable of eliminating traditional oriental doctors' subjectivity, collecting objective results of pulse diagnosis using sensors capable of detecting signals more accurately than humans' senses, and allowing examinees' pulsation to be viewed objectively has been carried out.

A representative example of conventional pulse taking devices is shown in FIGS. 4a and 4b. More particularly, a pulse taking device using a fixed support (Korean Unexamined Patent Publication No. 10-1994-0010974), a pulse taking device using a cuff (Korean Patent No. 10-1997-0005238), a pulse taking device using a piezoelectric sensor (Korean Patent No. 0344211), and a pulse taking device using an array sensor (Korean Utility Model Registration No. 0261625), shown in FIGS. 5a and 5b, have been disclosed.

Furthermore, Korean Patent No. 0672083 discloses a pulse wave analyzing method using an array pressure sensor, and the analyzing method enables an examinee's pulse wave information to be represented as variable conditions for variations in pressing force or the passage of time in a three-dimensional graph space.

Accordingly, it is estimated that the technical basis for detecting pulse condition information with relative accuracy at an examinee's pulse taking position and 3-dimensionally displaying results of the detection via an output device by combining the previously developed pulse taking device with the 3-dimensional pulse condition information analytic method has been established.

Meanwhile, most previously developed pulse diagnostic pulse taking devices provide bio-impedance measurement results, obtained simply through piezoelectric sensors or the like, in the form of an output screen without bibliographical or clinical considerations with regard to pulse conditions used differently for respective purposes, respective preferences, respective symptoms and respective diseases, and thus it is impossible in practice to analyze an examinee's pulse diagnotic information, measured at a pulse-taking location, within the pulse diagnostic systems, therefore the pulse diagnostic information is of significance only as a reference that is used before an actual traditional oriental doctor's clinical diagnosis.

More particularly, the conventional pulse taking devices have been developed with an emphasis on the improvement of the performance of a pulse-taking sensor and a pressing unit, there is a limitation in that it is impossible to make an automatic diagnosis on an examinee's pulse condition within a pulse diagnostic system using such a pulse taking device or pulse taking device, even though the pulse diagnostic system is combined with a 3-dimensional analysis technique for pulse condition information.

Furthermore, in order to acquire an examinee's accurate pulse diagnostic information, the determination of three locations, namely, the Cun, Gu and Chi locations, which are pulse-taking locations, and the operational control of the pulse-taking sensor must be considered as important factors in the design of a pulse taking device.

The process by which a traditional oriental doctor takes a pulse is described below in detail. First, an examinee's Gu pulse-taking location is determined, and then the Cun and Chi pulse-taking locations are determined based on the Gu pulse-taking location. Many traditional oriental doctors have expressed various opinions on the lengths of the Cun, Gu and Chi pulse-taking portions. Specifically, Nan Jing (難經) defined the distance of the Gu portion as 1 Fen (分) and determined the total length of the three Cun, Gu and Chi pulse-taking portions to be 1 Cun and 9 Fens, while Wang Shuhe (王叔和), Yang Xuancao (楊玄操) and Wang Bing (王氷) defined the length of the Gu pulse-taking portion as 10 Fens and determined the total length of the three Cun, Gu and Chi pulse-taking portions to be 3 Cuns (refer to FIG. 5). Furthermore, Huangfu Mi (皇甫謐) divided the total length of the Cun, Gu and Chi pulse-taking portions, that is, 1 Cun and 8 Fens, in a ratio of 6:6:6, and, according to the commentary of Yang Xuancao (楊玄操), Huatuo (華陀) divided a total of 1 Cun and 9 Fens in a ratio of 8:3:8. Gao Yangsheng (高陽生) divided a total of 3 Cuns in a ratio of 10:10:10 in Wang Shuhe's Secret Instructions on the Pulse (王叔和脈訣), and Sun SsuMiao (孫思邈) divided 1 Cun and 9 Fens in a ratio of 7:6:6. Based on Wang Shuhe's Secret Instructions on the Pulse (王叔和脈訣), Yang Xuancao (楊玄操) and Wang Bing (王氷) divided a total of 3 Cuns in a ratio of 10:10:10 and thus defined the Cun, Gu and Chi pulse-taking portions. Although the traditional oriental medical doctors' opinions on the lengths of the three portions varied with the times, most traditional oriental medical doctors have considered each of the lengths of the Cun, Gu and Chi pulse-taking portions to be one Cun since the assertion of Yang Xuancao (楊玄操) and Wang Bing (王氷).

Since 1 Cun is actually about 20 mm according to a well-known measurement conversion factor, the total length of the three Cun, Gu and Chi pulse-taking portions is 60 mm upon measurement conversion. However, when a pulse-taking posture is naturally assumed, the distance between the pad of the index finger and the pad of the ring finger is about 26 mm according to measured data, so that the distance forms a range within which a pulse cannot be taken using a traditional three-finger pulse diagnostic method. Accordingly, in actual clinical situations, the assertion in which each of the lengths of the Cun, Gu and Chi pulse-taking portions is 1 Cun is disregarded, and traditional oriental doctors arbitrarily take pulses using the three-finger pulse diagnostic method.

In modern traditional oriental medicine, there are different opinions on the relative locations and distances between the Cun, Gu and Chi pulse-taking locations. The key to the determination of three pulse-taking locations, that is, the Cun, Gu and Chi pulse-taking locations, is to determine the distances from the central Gu pulse-taking location to the Cun and Chi pulse-taking locations so as to determine the Cun and Chi pulse-taking locations based on the central Gu pulse-taking location.

Although the definitions of the relative locations and distances between the Cun, Gu and Chi pulse-taking locations are very important factors in the extraction of an examinee's pulse condition information, as described above, the conventional pulse taking devices are designed such that, when the Gu pulse-taking location, which is a reference location for pulse taking, is determined via an examiner's palpation or using an instrument based on the detection of the eminent head of the radius, pulse condition information at the Cun, Gu and Chi pulse-taking locations is measured using a plurality of pulse-taking sensors arranged at predetermined intervals, or pulse condition information at the Gu pulse-taking location is first measured based on a predetermined distance value, movement to the Cun and/or Chi pulse-taking location is made, and then pulse condition information is collected.

However, the pulse taking device, designed as described above, has a problem in that the measurement process must be repeated because there is a strong possibility that pulse diagnotic information will be collected at pulse-taking locations that do not coincide with the concept of the Cun, Gu and Chi pulse-taking locations described in the original text, and thus it will not be possible to acquire accurate and reliable results in the actual process of measuring pulse condition information.

Moreover, pulse diagnostic analytic algorithms for pulse condition analysis, which are provided in either conventional pulse diagnostic devices or pulse taking devices, do not provide highly reliable pulse diagnostic analysis results because they have not been subjected to a process of designing output variables based on the physical consideration of the definitions of pulse conditions in light of traditional oriental medicine and a process of performing quantification based on clinical data.

More particularly, FIG. 6a shows a representative example of a conventional "pulse diagnostic analytic system", and FIG. 6b shows a flowchart showing "the flow of floating pulse and collapsing pulse analysis" in the pulse diagnostic analytic system. As seen from FIGS. 6a and 6b, the conventional pulse diagnostic systems do not provide sufficient analysis criteria for examinees' pulse condition information (for example, measured pulse pressures) collected by pulse diagnostic devices, that is, a clear basis for pulse condition diagnosis through the application of quantified output variables and determination logic based on the variables.

That is, since it is difficult to carry out systematic research through cooperation between experts in related fields, such as traditional oriental medicine experts and mechanical engineers, due to the special circumstances of the development of pulse diagnostic devices and pulse taking devices, it is true that there exists an inherent limitation, in which consideration in the light of traditional oriental medicine and the design and quantification of output variables based on clinical data, which are requirements essential for the design and improvement of the performance of pulse diagnostic devices and pulse diagnostic systems, are neglected.

The conventional pulse diagnostic devices and pulse diagnotic systems based on the diagnostic algorithms, which are not based on based on the physical consideration of the definitions of pulse conditions in light of traditional oriental medicine and clinical data, as described above, have limitations in that the utility thereof is very low from the actual clinical point of view and the reliability thereof is very low from the point of view of the objectivity and reproducibility of pulse taking results diagnosis.

In order for the conventional pulse diagnotic systems, including conventional pulse diagnotic devices, to be developed into automatic pulse diagnotic systems, rather than mere devices for simply outputting the results of bio-impedance measurement, various attempts to quantify output variables, such as the design of output variables based on the physical consideration of pulse conditions defined in traditional oriental medicine classics, the improvement of the conventional pulse diagnotic systems based on the designed output variables, the collection of clinical data produced by the improved pulse diagnotic systems, and the statistical analysis of the collected clinical data, are required.

As a result, a series of processes of designing output variables in conformity with the characteristics of respective principal pulse conditions, defined in old books regarding traditional oriental medicine, quantifying the output variables, correcting and supplementing the output variables based on clinical data, and determining the output variables is essentially required for the improvement of the pulse diagnotic systems.

DISCLOSURE

Technical Problem

The present invention is intended to provide an automatic diagnotic system capable of accurately determining pulse-taking locations, that is, the Cun, Gu and Chi pulse-taking locations, which must be found in advance in order to achieve the accurate detection and analysis of information about an examinee's accurate pulse condition.

The present invention is intended to provide an automatic pulse diagnotic system, in which a previously disclosed pulse taking device and a three-dimensional analysis technique for pulse condition information are combined with output variables quantified based on a large amount of clinical data, thereby providing objective and highly reliable pulse diagnotic results.

The present invention is generally intended to provide a system for diagnosing principle pulse conditions defined in traditional oriental medicine classics, particularly a deficient pulse and an forceful pulse, and, more particularly, is intended to provide a system for diagnosing a deficient pulse and an forceful pulse, including a pulse diagnotic device for measuring pulse condition information at an examinee's Cun, Gu and Chi pulse-taking locations on his or her wrist using one or more pulse-taking sensors, a deficient pulse and forceful pulse determining device operably connected to the pulse diagnotic device, and configured to analyze the pulse pressure information measured by the pulse diagnotic device, to calculate a quantified deficiency/forceful coefficient and to determine whether the pulse of interest is a deficient pulse or an forceful pulse, and an output device connected to the determining device and configured to display the results of the determination.

Technical Solution

In order to accomplish the above objects, the present invention provides a system for diagnosing a deficient pulse and an forceful pulse, including a pulse diagnotic device configured to measure pulse condition information at an examinee's Cun, Gu and Chi pulse-taking locations on his or her wrist using one or more pulse-taking sensors, a deficient pulse and forceful pulse determining device operably connected to the pulse diagnotic device, and configured to analyze the pulse pressure information measured by the pulse diagnotic device, to calculate a quantified deficiency/forceful coefficient and to determine whether the pulse of interest is a deficient pulse or an forceful pulse, and an output device connected to the determining device and configured to display the results of the determination.

Advantageous Effects

A system for diagnosing a deficient pulse and an forceful pulse according to the present invention has output variables that are quantified through the physical consideration of the concept of the pulse condition of traditional oriental medical classics, the design of the output variables based on the consideration, the collection of high-quality traditional oriental medical clinical data based on clinical test methodology, the statistical analysis of the collected data, and the correction and supplementation based on a massive clinical DB, thus providing objective and highly reliable results of the diagnosis of a deficient pulse and an forceful pulse.

A floating/collapsing coefficient for diagnosing a deficient pulse and an forceful pulse and an analytic algorithm using the floating/collapsing coefficient, which are disclosed by the present invention, can be easily applied to previously developed pulse diagnotic apparatuses or pulse condition analytic apparatuses, therefore the period of research in the field of traditional oriental medicine, which requires a long period for the collection of clinical data, can be shortened, and it is expected that a pulse condition analytic method that maximally reflects clinical doctors' opinions can be implemented.

Furthermore, the system of the present invention can technically improve the efficiency of processing of bio-signals and the performance of automatic diagnosis in the field of pulse diagnosis, and can contribute to the objective description of bio-information. Through this, patients can be monitored using traditional Korean medical diagnosis equipment, so that a system for the clinical evaluation of traditional oriental medicine can be set up, and scientific and quantitative approaches to the theories of traditional oriental medicine can be made.

From the point of view of the economy and industry, medical costs can be reduced through the promotion of health and the early detection of diseases, and the present invention can contribute to the basis on which traditional oriental medicine enters the home medical market as the ubiquitous medical market is expanded.

Through the combination of engineering, natural science and traditional oriental medicine, the present invention can contribute to the establishment of a system for the development of traditional Korean medical equipment and the expansion of the traditional Korean medical equipment market based on the establishment. More particularly, the present invention can contribute to a system for traditional Korean medical clinical evaluation, thereby promoting the development of the traditional Korean medical equipment industry, including the pulse taking device industry, and improving the competitiveness thereof.

From the point of view of society, the present invention provides a basis for basic research into traditional oriental medicine, therefore it is expected that the present invention can contribute to the establishment of a scientific traditional oriental medicine practice and to the expansion and popularization of health awareness and methods of promoting health based on traditional oriental medicine.

DESCRIPTION OF DRAWINGS

FIG. 2a is a diagram showing 'the anatomical arterial circulatory system', and FIG. 2b is a diagram showing 'traditional pulse-taking locations in traditional oriental medicine';

FIG. 3 is a diagram showing the 'Cun', 'Gu' and 'Chi' pulse-taking locations, and a pulse taking process performed by a traditional oriental doctor;

FIG. 4a is a diagram showing an example of a conventional pulse diagnostic device, and FIG. 4b is a diagram showing another example of the conventional pulse diagnostic device;

FIG. 6a is a diagram showing a representative example of a previously developed pulse diagnostic system, and FIG. 6b is a flowchart showing the flow of the pulse diagnostic analysis of the pulse diagnostic system, which shows a process of floating and collapsing pulse analysis as an example;

BEST MODE

Figure 1:
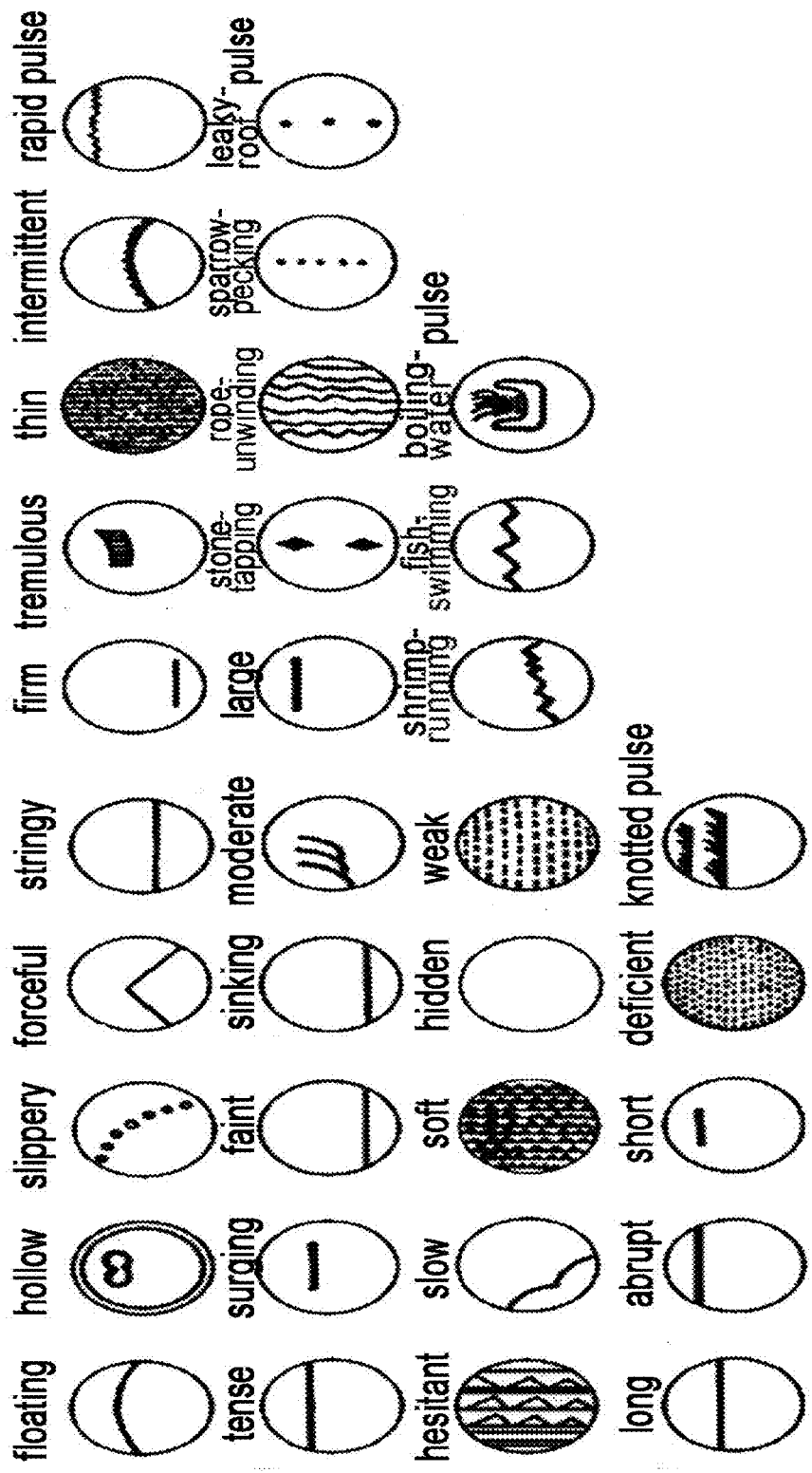
FIG. 1 is a diagram showing the 33 pulse condition chart of Chabingzhinan (察病指南, which stands for the title of "monitoring diseases and directing south")
Figure 5:
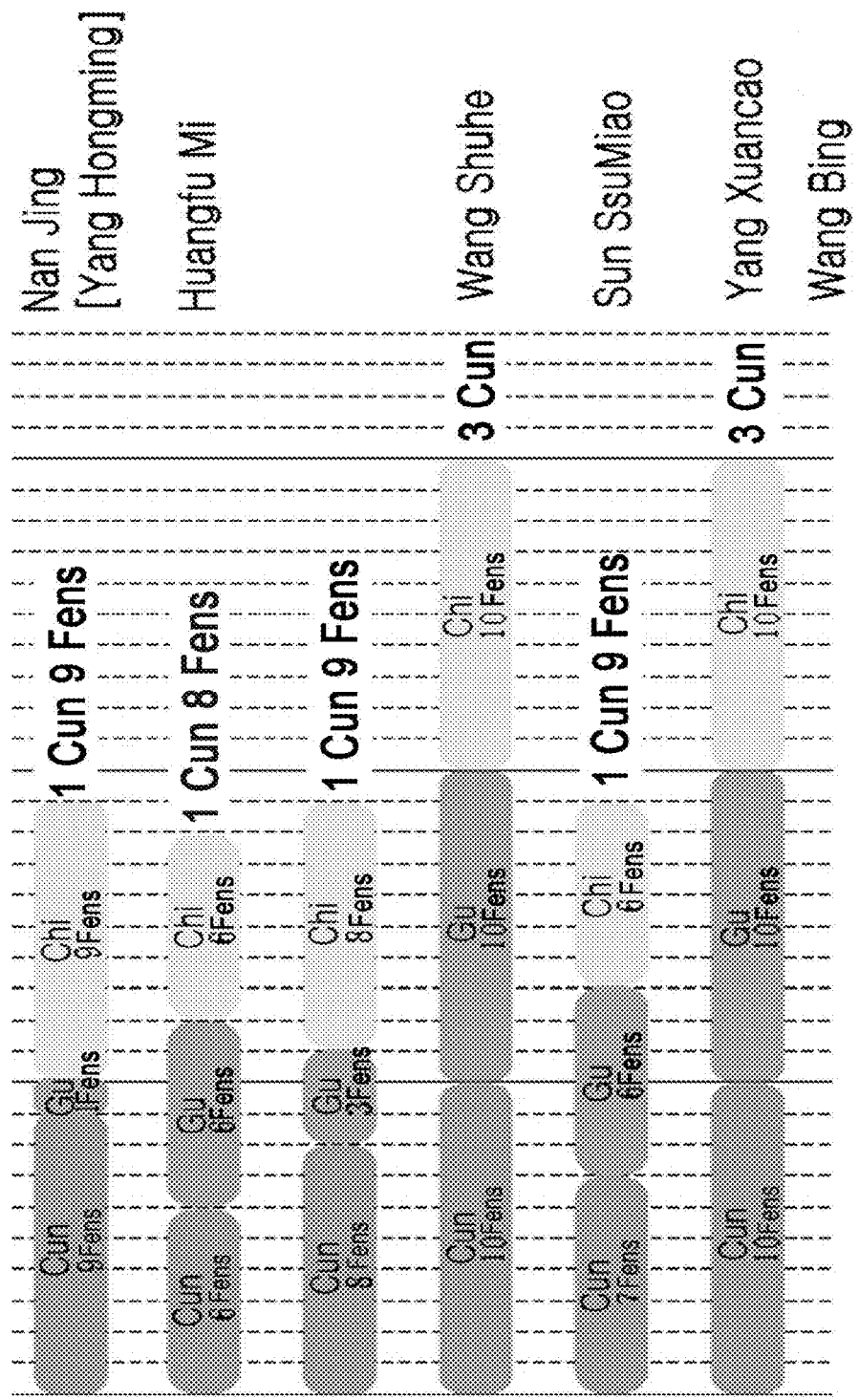
FIG. 5 is a diagram showing 'opinions on the relative locations and lengths of the three Cun, Gu and Chi pulse-taking locations'.

A system for diagnosing a deficient pulse and an forceful pulse according to the present invention will be described below in detail with reference to the accompanying drawings below.

The system for diagnosing a deficient pulse and an forceful pulse according to the present invention includes a pulse diagnostic device configured to measure pulse condition information at an examinee's Cun, Gu and Chi pulse-taking locations on his or her wrist using one or more pulse-taking sensors, a deficient pulse and forceful pulse determining device operably connected to the pulse diagnostic device, and configured to analyze the pulse pressure information measured by the pulse diagnostic device, to calculate a quantified deficiency/forceful coefficient and to determine whether the pulse of interest is a deficient pulse or an forceful pulse, and an output device connected to the determining device and configured to display the results of the determination (refer to FIGS. 7a and 7b).

The pulse diagnostic device of the system for diagnosing a deficient pulse and an forceful pulse according to the present invention will be described in detail below.

The pulse diagnostic device according to the present invention includes a wrist holding unit for securing an examinee's wrist, a pulse-taking sensor for coming into contact with the inner surface of the examinee's wrist, measuring pulse pressures at three Cun, Gu and Chi pulse-taking locations, and outputting corresponding electrical signals, a lateral transfer unit for enabling the lateral transfer of the pulse-taking sensor, a vertical transfer unit for adjusting pressures applied by the pulse-taking sensor to the examinee's pulse taking portions, in steps, a microprocessor for controlling the lateral and vertical locations of the pulse-taking sensor, an amplifier for amplifying analog signals from the pulse-taking sensor, a filter unit for filtering out noise from the amplified analog signals an A/D conversion unit for converting the filtered, amplified analog signals into digital signals, and a communication interface for communicating with a deficient pulse and forceful pulse determining device.

More particularly, the pulse diagnostic device according to the present invention may be a pulse diagnostic device that includes a plurality of pressure sensors, a wrist holding unit, an amplifier, a filter unit and an A/D conversion unit, and that eliminates excessive signal components attributable to the vertical movement of an examinee's wrist, so that accurate pulse pressures or pulse wave forms can be extracted at the examinee's pulse-taking locations in pressing steps assigned to the pressure sensors. Examples of the pulse diagnostic device include a pulse diagnostic apparatus (Korean Patent No. 0464806) and a pulse taking device (Korean Patent No. 0344211).

It is preferred that the pulse-taking sensor of the present invention be pressure sensors, including pressure detection elements, or an array sensor, including semiconductor pressure sensors. Examples of such a pulse-taking sensor include a typical array sensor (Korean Utility Model Registration No. 261624) and a semiconductor array sensor (Korean Utility Model Registration No. 2784313).

Figure 10:
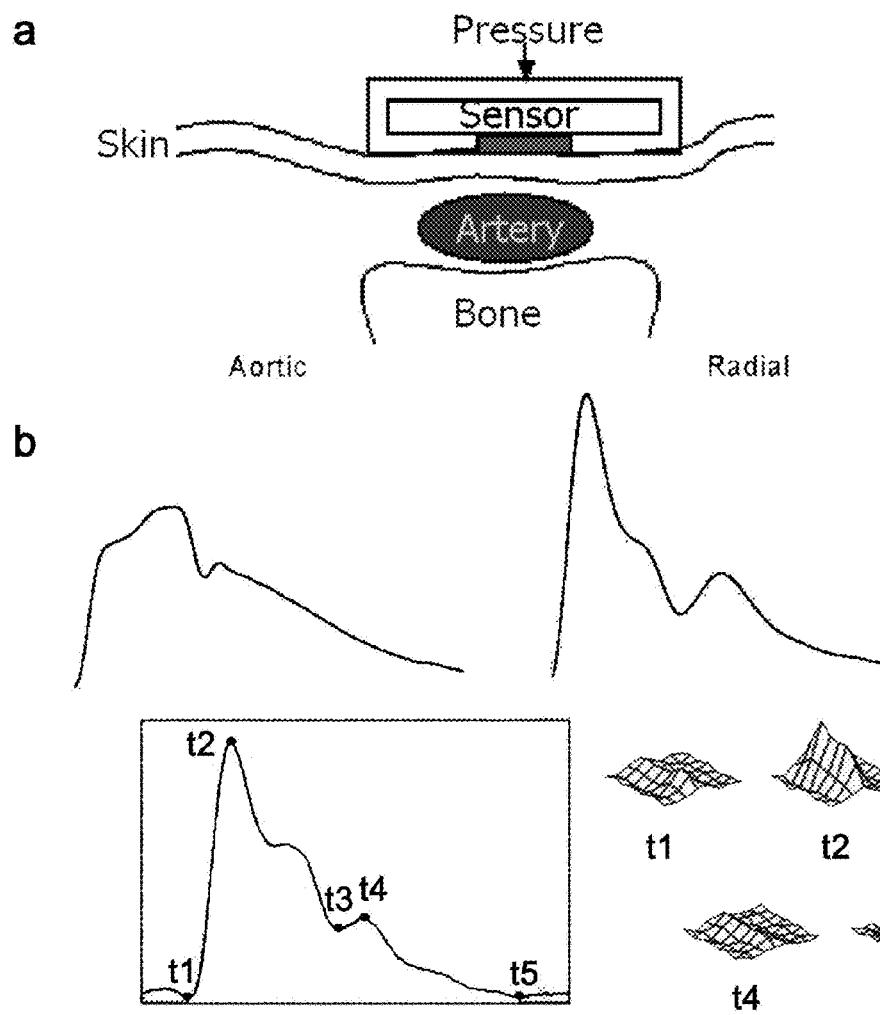
FIG. 10a is a diagram showing 'a pulse-taking sensor used at a pulse-taking location and an example of the measurement of a pulse condition using the pulse-taking sensor'.
FIG. 10b is a diagram showing 'the results of the measurement of a pulse condition using a single sensor and the results of the measurement of a pulse condition using a multichannel array sensor'.

More particularly, with regard to the pulse-taking sensor, it is preferable to measure pressures using a plurality of pressure sensors or an array sensor, including semiconductor pressure sensors, rather than measuring pressures at the Cun, Gu and Chi pulse-taking locations using a single pressure sensor, so as to improve the sensitivity of measurement and 3-dimensionally analyzing extracted pulse condition information (refer to FIGS. 10a and FIG. 10b).

FIG. 10b shows a representative example of signals measured at time points t1~t5 by a single sensor and a representative example of signals measured at time points t1~t5 by a multichannel array sensor. From the drawing, it can be seen that the single sensor can measure a pulse wave signal only at a single location, while the multichannel array sensor has an advantage of measuring pulse wave signals simultaneously at a plurality of locations. Accordingly, in a preferred embodiment of the present invention, the pulse-taking sensor may be a multichannel array sensor.

Figure 11:
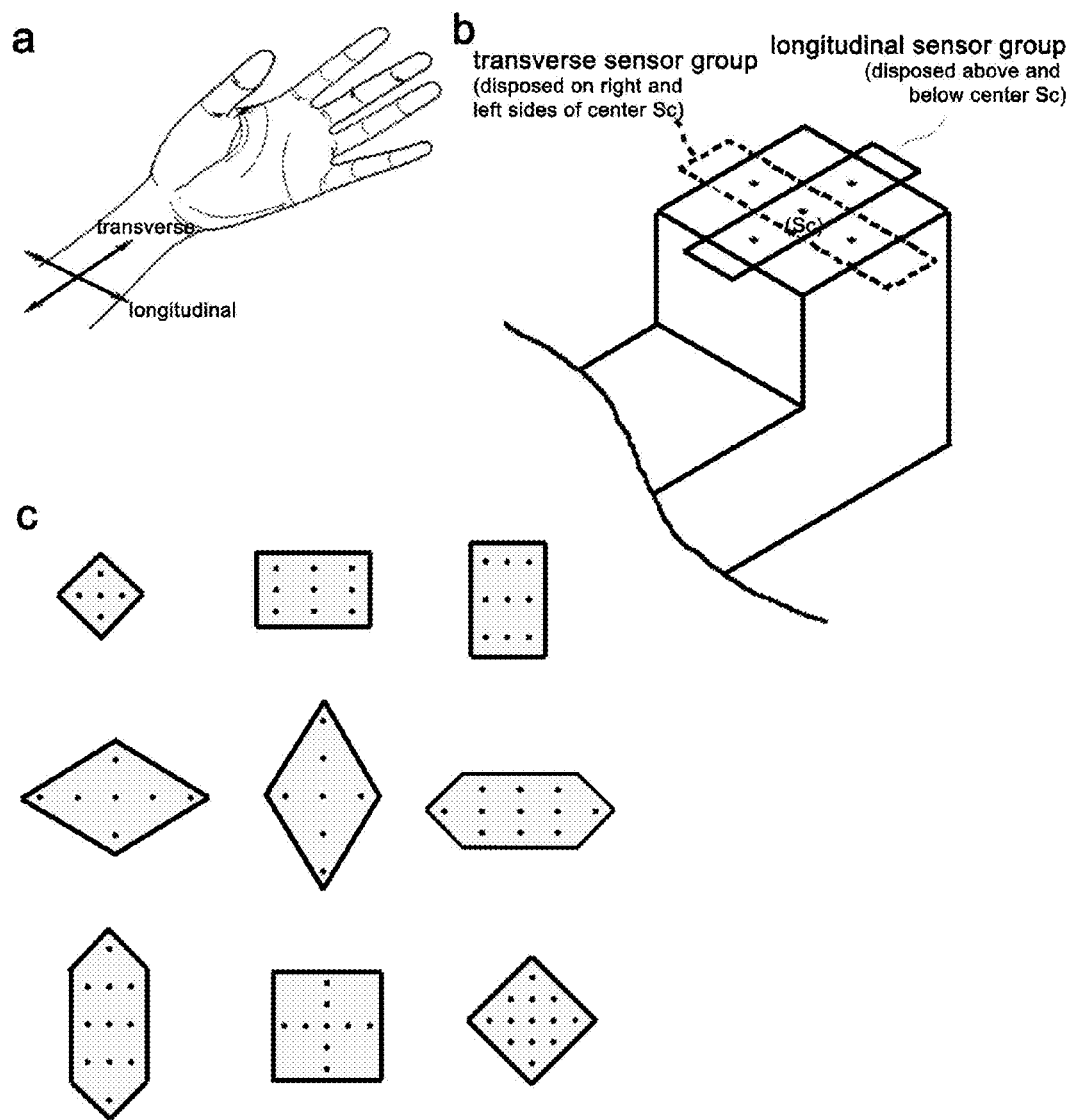
FIG. 11a is a view showing 'the directions of contact of the array sensor of the present invention with a pulse-taking portion'.
FIG. 11b is a view showing 'the longitudinal sensor group and transverse sensor group of the array sensor' according to the present invention.
FIG. 11c is a view showing 'various arrangements of the array sensor' according to the present invention.
Figure 12:
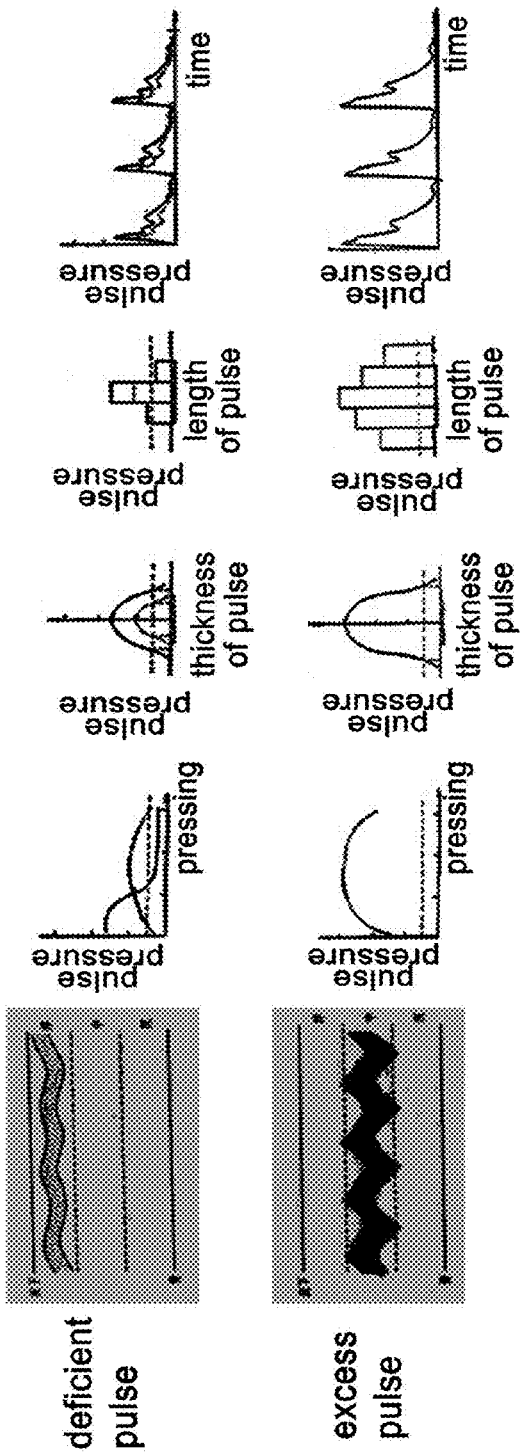
FIG. 12 is a diagram schematically showing 'the definitions of a deficient pulse and an forceful pulse in traditional oriental medicine, an output parameter, and output variables'.

When a direction extending from the wrist to the hand is defined as a 'transverse direction' and a direction extending from the radius of the wrist across the wrist is defined as a 'longitudinal direction', the array sensors include both a transverse sensor group, which comes into contact with the Cun, Gu and Chi pulse-taking locations in a transverse direction and measures pulse pressures, and a longitudinal sensor group, which comes into contact with the Cun, Gu and Chi pulse-taking locations in a longitudinal direction and measures pulse pressures. It is preferred that 5 to 13 semiconductor pressure sensors be disposed in a cross, square, rectangular, diamond or hexagonal arrangement (refer to FIG. 11).

FIG. 11b discloses a pulse-taking sensor in which five semiconductor pressure sensors are disposed in a cross arrangement from the point of view of 3-dimensional orientation and measurement efficiency, as a preferred embodiment of the present invention. More particularly, pressure sensors located to the right and left of a center sensor (Sc), located at the center of the cross sensor arrangement, are defined as a transverse sensor group, while pressure sensors located above and below the center sensor Sc are defined as a longitudinal sensor group.

In the pulse-taking sensor shown in FIG. 11b, the thickness of a pulse can be estimated using the values of the three longitudinal sensors, and the length of a pulse can be estimated using the values of the three transverse sensors. Since the thickness of a pulse is the basis for determining a large pulse or a fine pulse, the arrangement of five semiconductor pressure sensors in a cross form is the arrangement of the least number of sensors that enables the measurement of the thickness of a pulse that is required in order to detect a large pulse or a fine pulse.

FIG. 11c shows various examples of the implementation of array sensors according to the present invention. As long as both the transverse sensor group and the longitudinal sensor group, disclosed in FIG. 11b, are included, a square, rectangular, diamond or hexagonal arrangement may be selected by adding sensors.

The pulse-taking sensor of the present invention acquires pulse condition information while adjusting pressing force, applied to the pulse-taking locations, in 3 to 10 steps.

It is most appropriate that the pressing force be adjusted in five steps and then be used. If the number of pressing steps is small, the distinguishing ability of the deficiency/forceful coefficient is low. In contrast, if the number of pressing steps is large, accurate measurement can be made, but excessive time may be consumed.

More particularly, the pulse-taking sensor measures a pressure at each pulse-taking location while increasing the pressing force from a first step to a fifth step. In this case, the pressing force at the time that a measured pulse pressure is equal to or higher than a predetermined value is defined as the value of the first step, the pressing force at the time that the pulse pressure increases and then decreases to a value equal to or lower than the predetermined value is defined as the value of the fifth step, the defined pressing force range is divided into equal intervals, and then pressing is performed in equal interval steps.

The location control microprocessor of the present invention controls the lateral transfer unit and vertical transfer unit for moving the pulse-taking sensor, sets a range, from a pressing force at the time that the pulse pressure is measured and taken as a predetermined threshold value to a pressing force at the time that the pulse pressure increases and then decreases to the predetermined threshold value, as the range of the pressing force applied to the pulse-taking sensor, divides the range of the pressing force into equal intervals, and controls the vertical transfer unit using pressing means for measuring pulse pressures while increasing the pressing force in respective steps.

More particularly, it is preferred that the threshold value range from 1 to 5 mmHg. It is most preferable that the threshold value be 3 mmHg.

Furthermore, the location control microprocessor of the present invention may further include pulse-taking location determination means that takes the Cun, Gu and Chi pulse-taking locations, described in the original Chinese medicine text, into consideration and reduces the time taken to measure an examinee's pulse condition information.

It is preferred that the pulse-taking location determination means according to the present invention include 1) a first transfer module for determining a location spaced apart from the predetermined Gu pulse-taking location in the left-lateral direction (in the distal direction from the wrist) by a preset moving distance for the Cun pulse-taking location, that is, 11.4 mm, to be the Cun pulse-taking location, 2) a returning module for returning the pulse-taking sensor to the predetermined the Gu pulse-taking location after the measurement of pulse pressures at the Cun or Chi pulse-taking location, and 3) a second transfer module for determining a location spaced apart from the predetermined Gu pulse-taking location in the right-lateral direction (in the proximal direction from the wrist) by a preset moving distance for the Chi pulse-taking location, that is, 14.9 mm, to be the Chi pulse-taking location.

More particularly, the moving distances for the Cun and Chi pulse-taking locations, set to specific numerical values, are based on the results of actual measurement for an examinee. That is, as a result of measurement of 78 examinees, it is determined that the average of the distances from the examinees' eminent heads of the radiuses to the wrist joints is 19.0 mm and the average of the distances from the eminent heads of the radiuses to the elbow joints is 229.2 mm. Accordingly, in a preferred embodiment of the present invention, the pulse-taking location determination means may be set such that, in the case where a rapid diagnosis is required, the Cun and Chi pulse-taking locations are determined using the preset moving distances for the Cun and Chi pulse-taking locations.

It is preferred that the pulse-taking location determination means of the present invention set different sensor locations for different examinees at the time of pulse taking at the Cun, Gu and Chi pulse-taking locations so as to more accurately perform the determination of pulse-taking locations.

In order to achieve the above-described purpose, the pulse diagnostic location determination means includes:

1) a distance information storage module for receiving and storing a distance value (a), measured from the eminent head of the radius to the wrist joint (between the scaphoid and the radius), and a distance value (b), measured from the eminent head of the radius to the elbow joint (between the radius and the humerus), the measurement being performed in a state in which an examinee holds the arm upright on a support surface, thereby taking a comfortable posture, and then raises the wrist somewhat so that the lower portion of the thumb is aligned with the wrist;

2) a first calculation module for calculating a moving distance for the Cun pulse-taking location using the distance value (a) from the storage module;

3) a second calculation module for calculating a moving distance for the Chi pulse-taking location using the distance value (b) from the storage module;

4) a first location determination module for receiving the distance value calculated by the first calculation module, moving the lateral transfer unit from the predetermined Gu pulse-taking location in a left-lateral direction (in a distal direction from the wrist), and determining the resulting location to be the Cun pulse-taking location;

5) a returning module for returning to the predetermined Gu pulse-taking location along the distance, calculated by the first calculation module, after completing the measurement of pulse pressure at the Cun pulse-taking location, achieved by the first location determination module and;

6) a second transfer module for receiving the distance value calculated by the second calculation module, moving the lateral transfer unit from the predetermined Gu pulse-taking location to the right (in a proximal direction from the wrist), and determining the resulting location to be the Chi pulse-taking location;

wherein the moving distance for the Cun pulse-taking location is 0.6*(a), and the moving distance for the Chi pulse-taking location is 0.065*(b).

More particularly, in a preferred embodiment of the present invention, the determination module may be set such that the lateral transfer unit first moves to the Chi pulse-taking location before moving to the Cun pulse-taking location, in which case the returning module returns from the predetermined Chi pulse-taking location to the predetermined Gu pulse-taking location by 0.065*(b), and then the first transfer module makes transfer and determines the Cun pulse-taking location.

Meanwhile, in a preferred embodiment of the present invention, the vertical transfer unit and the lateral transfer unit may be implemented using a multiaxial robot hand, and the location control microprocessor may be replaced with the operational control unit of the multiaxial robot hand.

More particularly, in a pulse taking device equipped with a multiaxial robot hand (50), the multiaxial robot hand (50) is provided with a pressure sensor (40), the pressure sensor acquires pulse condition signals, such as pulse pressure and a pulse waveform, at pulse-taking locations, the acquired pulse condition signals are amplified using an analog amplifier (60), noise is filtered out from the amplified analog signals by a filter unit (70), the filtered, amplified analog signals are converted into digital signals by an A/D conversion unit (80), the converted digital signals are processed by a signal processing unit (81) and sent to a communication interface unit (90), the communication interface unit sends the received signals to the deficient pulse and forceful pulse determining device (20), the multiaxial robot hand is laterally or vertically moved by the motor (51) of a motor driving unit (52), and the motor driving unit is controlled by an operation control unit (53).

Figure 7:
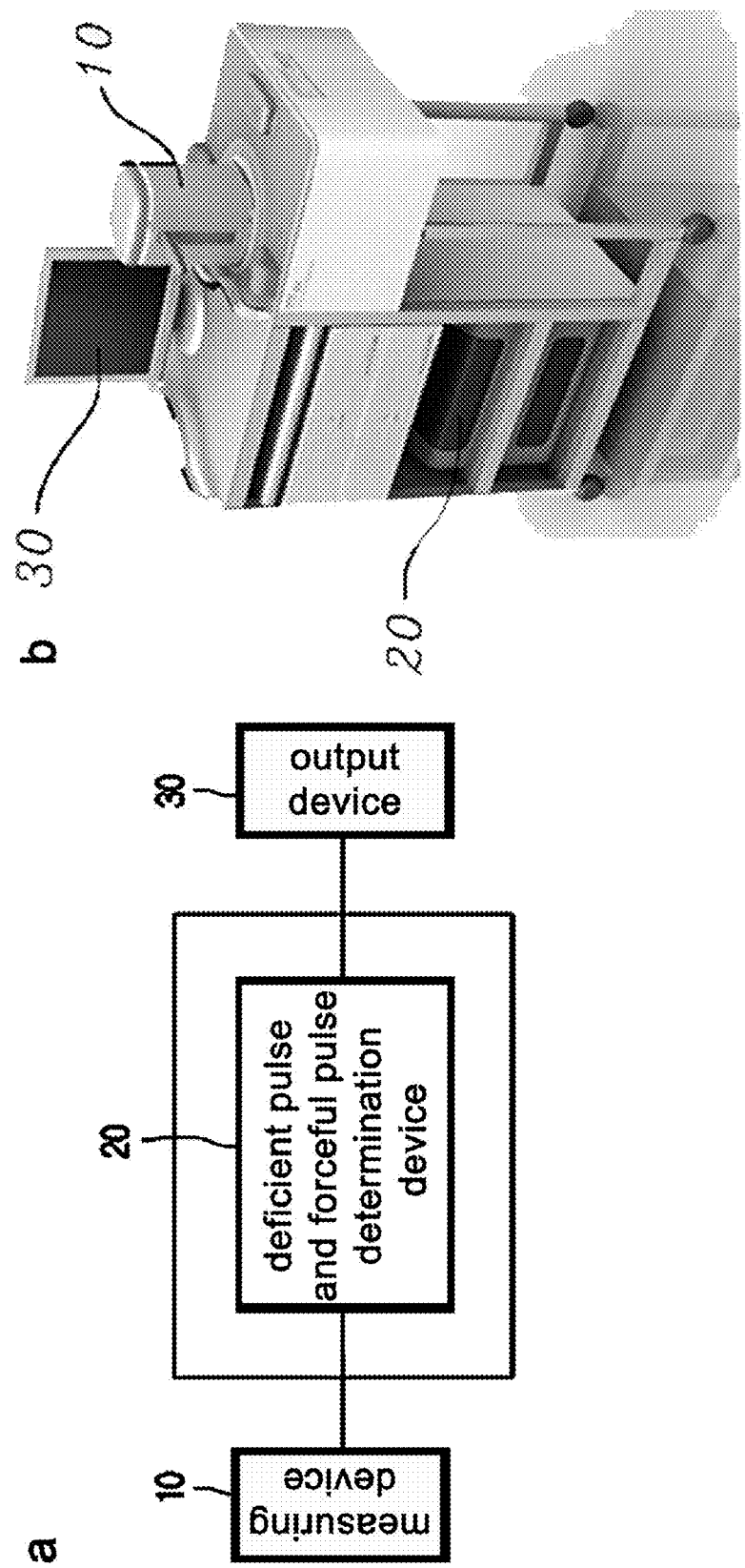
FIG. 7a is a 'schematic diagram of a deficient pulse and forceful pulse diagnotic system' according to the present invention.
FIG. 7b is a diagram showing 'a manufacturing model of the deficient pulse and forceful pulse diagnotic system' according to the present invention.
Figure 8:
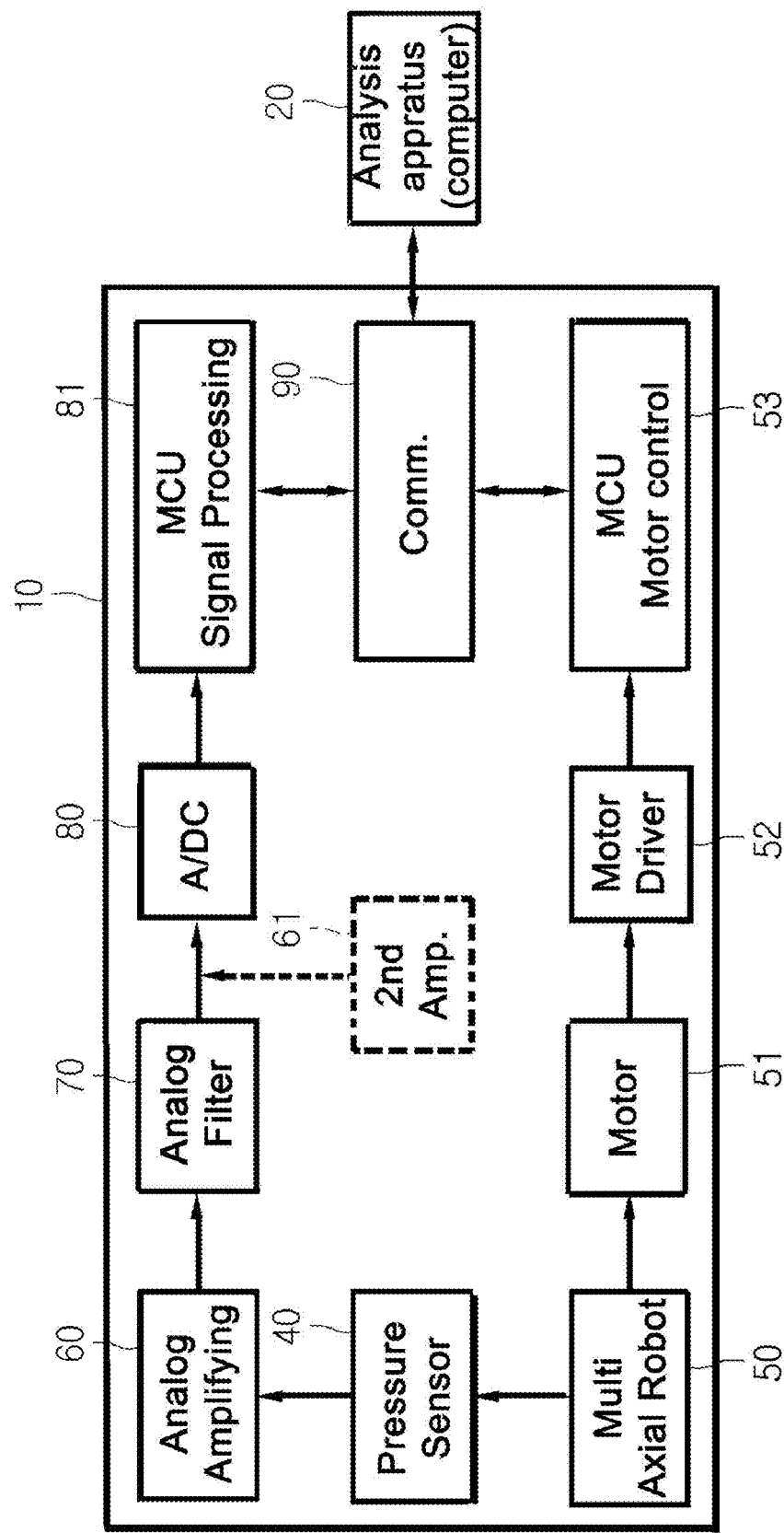
FIG. 8 is 'a block diagram of the deficient pulse and forceful pulse diagnotic system' according to the present invention.
Figure 9:
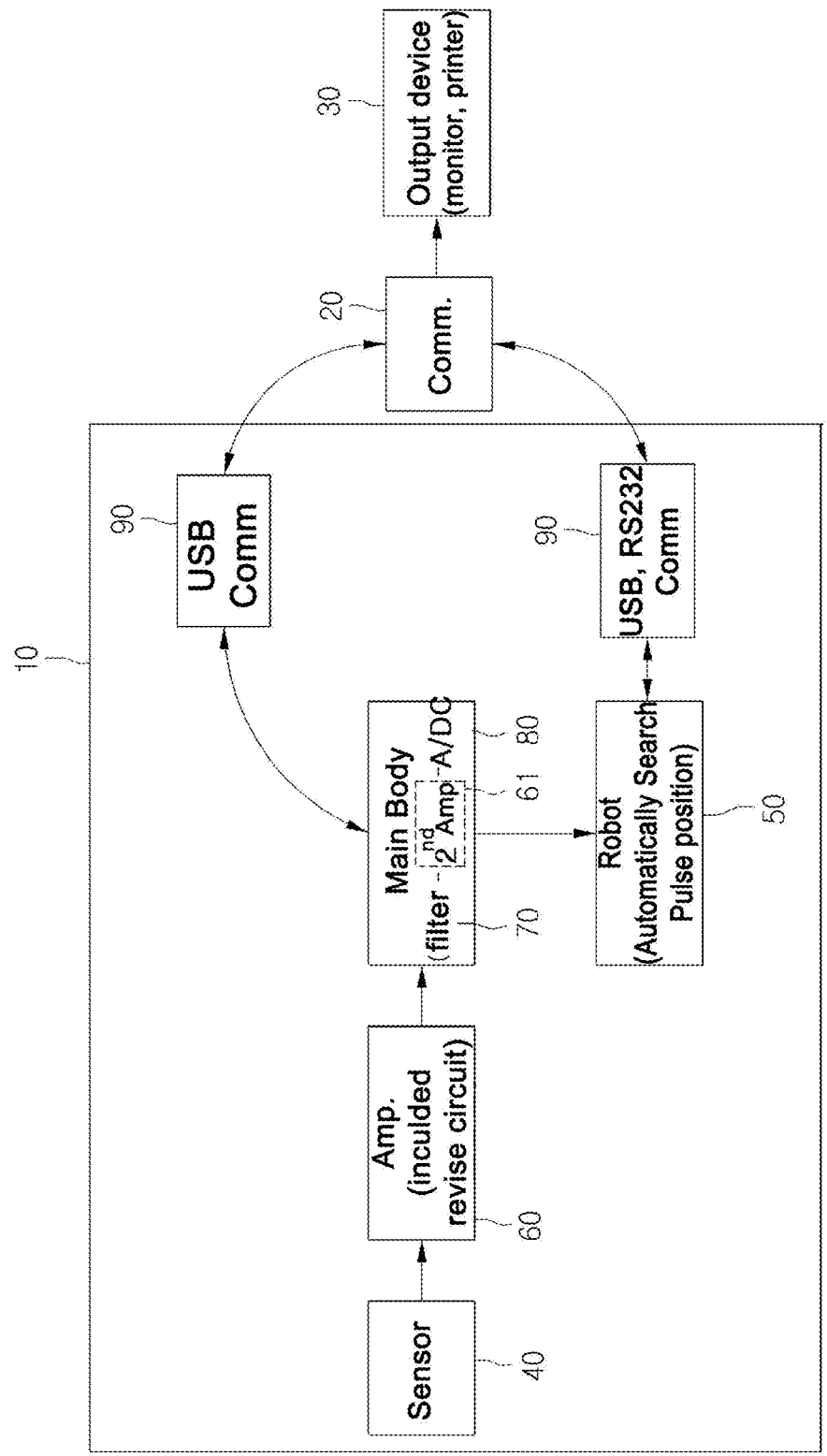
FIG. 9 is a diagram showing 'the flow of data in the deficient pulse and forceful pulse diagnotic system' according to the present invention.

A preferred embodiment of the pulse taking device equipped with the multiaxial robot hand according to the present invention is illustrated in FIG. 7, which is a block diagram of a "deficient pulse and forceful pulse diagnostic system". The flow of pulse diagnostic information in the deficient pulse and forceful pulse diagnostic system, in which the pulse taking device equipped with the multiaxial robot hand is included, is shown in FIG. 8.

More particularly, it is preferred that the multiaxial robot hand be provided with four axes in view of the movement of the pressure sensor and the flexible movement of the pressure sensor that supports desired contact at an examinee's pulse-taking locations. Furthermore, it is preferred that the signals, from which noise is eliminated by the filter unit, be amplified by a secondary amplifier (61) before being amplified by the A/D conversion unit.

In the pulse taking device of the present invention, it is preferred that the communication interface be a communication port, such as an RSC-232C, an IEEE 1394, a USB, or a Parallel port.

The deficient pulse and forceful pulse determining device of the present invention will be described in detail below.

The deficient pulse and forceful pulse determining device includes storage means for receiving and storing pulse pressure information, measured by the pressure sensor of the pulse taking device, which comes into contact with a pulse taking location; graphing means for receiving the stored pulse pressure information and converting variation in pulse pressure over time into a graph; selection means for selecting 'maximum pulse pressure during systole $h_P$', 'maximum pulse pressure during diastole $h_D$', 'inflection point time period between a first peak and a second peak during systole $t_Q$', 'systole time $t_C$', 'wave width $W_P$', 'systole area $A_S$' and 'diastole area $A_D$', and 'wave angle $\Theta_P$' from the graph as calculation variables; a deficiency/forceful coefficient calculation module for calculating a deficiency/forceful coefficient using the selected calculation variables; deficient and forceful pulse determination means for determining whether an examinee's pulse is a deficient pulse or an forceful pulse based on the calculated deficiency/forceful coefficient; and transmission means for transmitting the results of the deficient and forceful pulse determination to the output device. The deficient pulse and forceful pulse determining device may be a typical computer in which automatic deficient pulse and forceful pulse diagnostic software, implementing the respective means, is installed.

The 'maximum pulse pressure during systole $h_P$' according to the present invention is defined as the pulse pressure-axis maximum value of a first peak during systole (the time point at which the maximum artery pulse pressure is measured), while the 'maximum pulse pressure during diastole $h_D$' is defined as the pulse pressure-axis maximum value of a peak during diastole (the time point at which the maximum artery pulse pressure is measured).

The 'inflection point time period between a first peak and a second peak during systole $t_Q$' refers to the elapsed time from the time point at which the first peak during systole is created to the inflection point between the first peak and the second peak during systole, that is, the difference between the time-axis value of the inflection point Q between the first peak and the second peak during systole and the time-axis value of the point S at which the first peak during systole is created, while the 'time period during systole $t_C$' is defined as the elapsed time period from the time point at which a pulse pressure waveform during systole is created to the time point at which the valve of the main artery of the heart is closed, and thus the pulse pressure waveform during systole is extinguished, that is, the difference between the time-axis value of the inflection point C between the second peak during systole and the peak during diastole and the time-axis value of a point S at which a pulse pressure waveform during systole starts.

The 'wave width $W_P$' is defined as the difference 'b–a' between 'b' and 'a', when the x-axis coordinate value of the left of the points at which a straight line extending through the pulse pressure values that correspond to ⅔ of the representative pulse pressure $h_P$ meets the first peak during systole is designated as 'a', and the x-axis coordinate value of the point at which the straight line meets a straight line passing through the inflection point Q between the first peak and the second peak during systole and through the highest point P of the first peak during systole is designated as 'b'.

Figure 14:
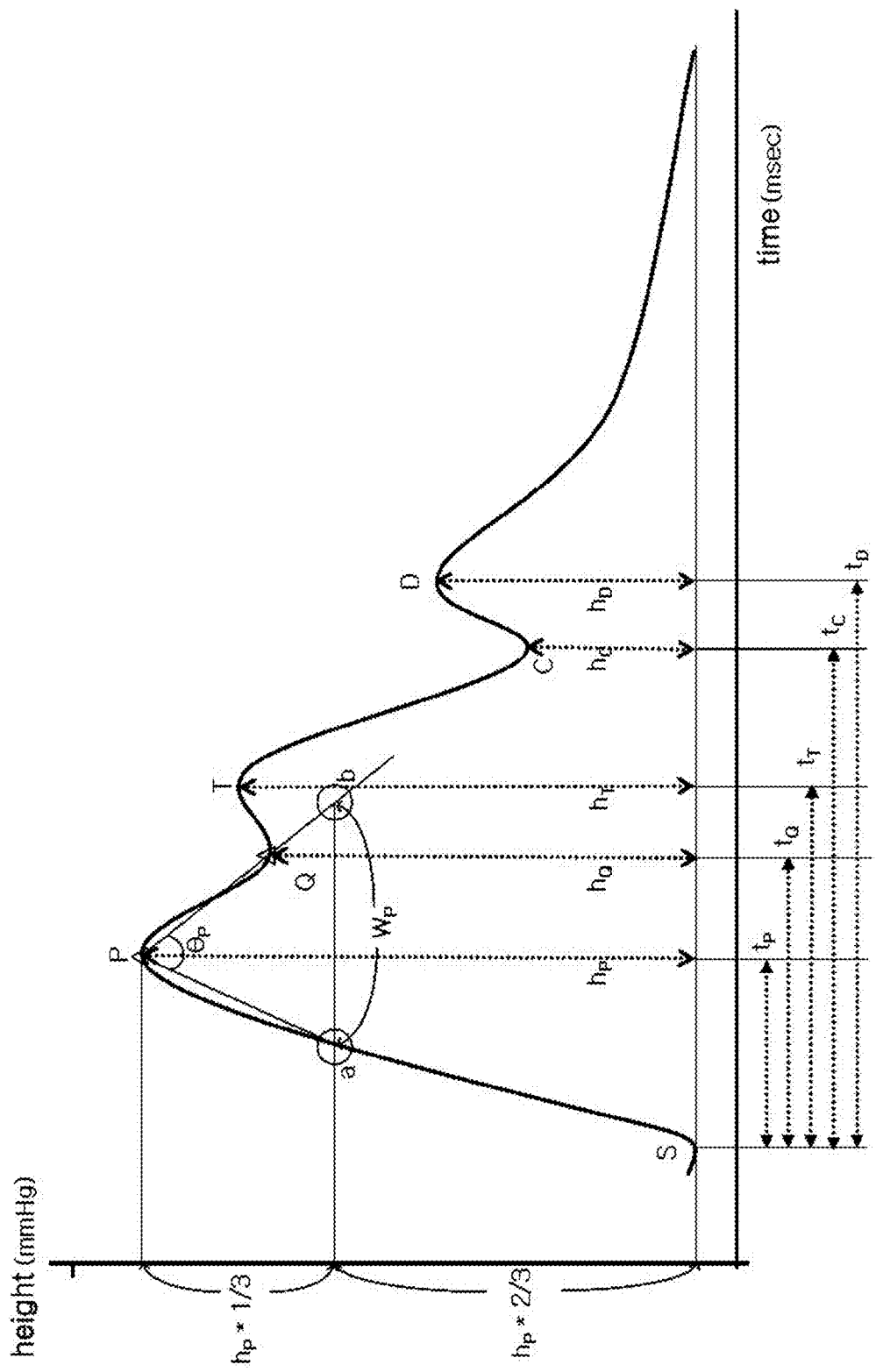
FIG. 14 is a 'graph showing a representative bit and related parameters', which are defined in an output variable quantification process according to the present invention.

The 'area during systole $A_S$' is defined as a value obtained by integrating pressures over a time period from the start point S of the pulse pressure waveform during systole to the inflection point C between the second peak during systole and the peak during diastole, 'the area during diastole AD at the Gu pulse-taking location' is defined as a value obtained by integrating pressures over the time period from the point C to the point S in the next cycle, and the 'wave angle $\Theta_P$ at the Gu pulse-taking location' is defined as an angle included between a straight line connecting the highest point P of the first peak during systole with 'a' and a straight line connecting the highest point P of the first peak during systole with 'b' (refer to FIG. 14).

More particularly, respective calculation variables according to the present invention refer to variables that exhibit statistically significant deviations from the averages of normal persons based on the analysis of the results of the deficient pulse and forceful pulse diagnoses of traditional oriental doctors in the cases of normal persons.

FIG. 14 is a pulse pressure waveform graph showing a typical example of a pressure signal, that is, a pulse wave, that is measured over time by the pressure sensor disposed at the Cun, Gu and Chi pulse-taking locations.

Since the Cun, Gu and Chi pulse-taking locations are located on the radius artery, variations in pulse pressure waveform occur with the contraction and expansion of the heart, with the result that unique pulse pressure wave forms during the systole and diastole of the heart are detected. The present inventors define calculation variables based on the definitions of respective points P, T, D, Q and C in the pulse pressure waveform graph of FIG. 14.

More particularly, in the pulse pressure waveform graph of FIG. 14, the systole is defined as the time period from the time point at which blood moves to the artery due to the contraction of the heart and an artery pulse pressure starts to increase, that is, the point S at which a pulse pressure waveform starts in the graph, to the time point at which the valve of the valve of the main artery is closed, that is, the time point C that distinguishes systole and diastole in a pulse pressure waveform from each other, and is shown as the 'time period during systole $t_C$' in the graph.

In the pulse pressure waveform graph, P is defined as the highest point of the first peak during systole, T is defined as the highest point of the second peak during systole, D is defined as the highest point of the pulse pressure peak during diastole, Q is defined as the inflection point between the first peak and the second peak during systole, and C is defined as the inflection point between the second peak during systole and the peak during diastole.

Accordingly, the 'maximum pulse pressure during systole $h_P$' is defined as the height at the time point (the pulse pressure-axis maximum pulse pressure value) at which the maximum artery pulse pressure is measured in the first peak during systole, the 'second pulse pressure during systole $h_T$' corresponds to the height at the time point (pulse pressure-axis maximum pulse pressure value) at which the maximum artery pulse pressure of the second peak, which is created during systole due to the influence of a reflected wave, is measured, and the 'maximum pulse pressure during diastole $h_D$' is defined as the height at the time point at which the maximum artery pulse pressure is measured in the pulse pressure peak during diastole (the pulse pressure-axis maximum pulse pressure value). $h_Q$ refers to the height (pulse pressure-axis maximum pulse pressure value) at the time point at which the first peak during systole is extinguished, or as the height (the pulse pressure-axis maximum pulse pressure value) at the time point at which the second peak during systole is created. $h_C$ is defined as the height (the pulse pressure-axis maximum pulse pressure value) at the time point at which the second peak during systole is extinguished or the height (the pulse pressure-axis maximum pulse pressure value) at the time point at which the peak during diastole is created.

It is preferred that the deficiency/forceful coefficient of the present invention be calculated using a discriminant expressed in the following Equation 1.

$$t = 1.273 + 0.014 \times h_P - 32.792 \times W_P \quad (1)$$

where the 'representative pulse pressure during systole $h_P$' is defined as the maximum pulse pressure value at the first peak during systole in a time versus pulse pressure variation graph, which is created by the graphing means. The 'wave width $W_P$' is defined as the difference 'b–a' between 'b' and 'a', when the x-axis coordinate value of the left of the points at which a straight line extending through the pulse pressure values that correspond to ⅔ of the representative pulse pressure $h_P$ meets the first peak during systole is designated as 'a', and the x-axis coordinate value of the point at which the straight line meets a straight line passing through the inflection point Q between the first peak and the second peak during systole and through the highest point P of the first peak during systole is designated as 'b'.

The determination means of the present invention calculates a Px value using the following Equation 2, and determines the pulse of interest to be a deficient pulse if the calculated Px value satisfies $0 \leq Px \leq 0.25$, to be an intermediate pulse if the calculated Px value satisfies $0.25 < Px < 0.75$, and to be an forceful pulse if the calculated Px value satisfies $0.75 \leq Px \leq 1.0$.

$$P_x = \frac{e^t}{1 + e^t} \quad (2)$$

where t is defined as the primitive value of the deficiency/forceful coefficient calculated using Equation 1.

Furthermore, the deficient and forceful pulse determining device of the present invention may further include conversion means for converting an examinee's deficiency/forceful coefficient value into a standard score calculated based on a clinical DataBase (DB), and representing the examinee's condition in terms of a percentage based on age or gender.

More particularly, the conversion means includes:
1) a storage module for receiving and storing pulse diagnotic information collected from a population of normal persons;
2) a calculation module for calculating a deficiency/forceful coefficient using the stored pulse diagnostic information;
3) an arrangement module for arranging calculated deficiency/forceful coefficients in descending order;

4) a distribution chart preparation module for preparing a distribution chart for the arranged deficiency/forceful coefficients; and 5) a quartile calculation module for calculating quartiles, indicating the relative positions occupied by the respective calculated deficiency/forceful coefficients, from the prepared distribution chart and converting the quartiles into standard scores.

More particularly, in order to diagnose the examinee's condition from various aspects, it is preferred that in step 3), deficiency/forceful coefficients be arranged according to age or gender.

Figure 17:
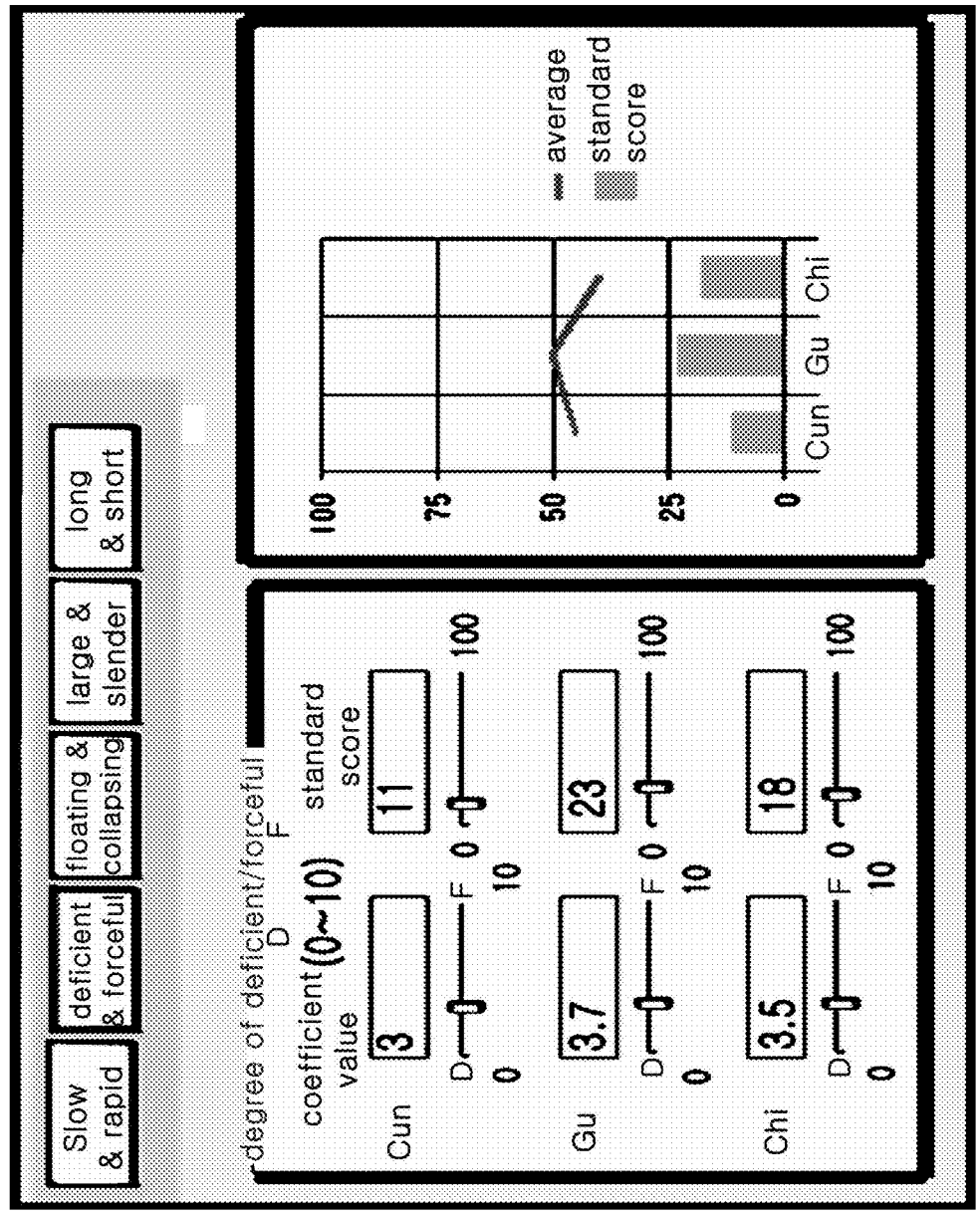
FIG. 17 is a diagram showing an example of the analytic window of the deficient pulse and forceful pulse analytic system according to the present invention.

FIG. 17 shows an example of the analytic window of the deficient pulse and forceful pulse diagnostic system according to the present invention. The lower right portion of the analytic window shows results indicating an examinee's standard score obtained through conversion by the conversion means of the present invention, and a level relative to the average of a normal person as percentages.

The deficient and forceful pulse determining device of the present invention may include an auxiliary storage device for storing the results of the determination of a deficient pulse or an forceful pulse in a file form and an input device for inputting patients' information.

The auxiliary storage device may be a floppy disk driver, or an internal or external hard disk, and the input device may be a keyboard.

The output device of the present invention can be connected to and communicate with the deficient pulse and forceful pulse determining device, and may be a typical monitor or printer.

Mode for Invention

A process of quantifying deficient pulse and forceful pulse output variables according to the present invention will be described in detail below.

Survey of Traditional Oriental Medical Documents and Extraction of Important Pulse Conditions The survey of traditional oriental medical documents were performed chiefly on the Yellow Emperor's Internal Classic (皇帝內徑), Nan Jing (蘭徑), the Pulse Classic (脈徑), and the Pulse Studies of Binhu 瀕湖脈學). Pulse conditions common to the descriptions of the documents were selected as principal pulse conditions. Based on the survey and the selection, the ranking of pulse conditions that were preferred and widely used in clinical situations and were frequently utilized for diagnosis and treatment was investigated through methods such as questionnaires and interviews. The results thereof are listed in the following Table 1.

TABLE 1

Results of survey of ranking of principal 'pulse conditions'

| Ranking | Pulse condition classification factor | Pulse condition |
|---|---|---|
| 1 | depth of location of pulse | floating(浮)/collapsing(沈) |
| 2 | number of pulses | slow(遲)/rapid(數) |
| 3 | magnitude of pulse | deficient(虛)/forceful(實) |
| 4 | width of pulse | slender(細)/large(大) or ful(洪) |
| 5 | length of pulse | long(洪)/short(短) |
| 6 | variation in pulse form | smooth(滑)/blocked(澀)/ taut(弦) |

TABLE 1-continued

Results of survey of ranking of principal 'pulse conditions'

| Ranking | Pulse condition classification factor | Pulse condition |
|---|---|---|
| 7 | variation in pulse rhythm | running(促)/knotted(結)/ intermitten(代) |

Based on the results of the survey of ranking, floating/collapsing, slow/rapid, deficient/excess, large/slender, and long/short pulses are determined to be ten principal pulses.

In the present invention, the output variables of the deficient and forceful pulses of the ten determined principal pulses are designed, and attempts to quantify the output variables are made.

Design of Output Variables of Deficient and Forceful Pulses

In order to develop a deficient pulse and forceful pulse diagnostic system based on traditional oriental medicine theories, output variables are designed.

As a result of the study of the definitions of deficient and forceful pulses in traditional oriental medicine and suitable physical quantities, output variables suitable for the deficient pulse and the forceful pulse are defined in the following Table 2.

TABLE 2

Definitions of deficient and forceful pulses and output variables

| Classification | Definition | Output variable |
|---|---|---|
| Deficient pulse | being floating, large and soft, and providing a touch of emptiness when being pressed lightly, a touch of insufficiency when being pressed strongly, and a touch of looseness a when the finger is lifted | intensity of pulse waves |
| Forceful pulse | having strength while being pressed lightly or strongly and providing touches of hardness and substantiality | |

More particularly, from the point of view of traditional oriental medicine, the deficient pulse is described as 'being floating, large and soft, and providing a touch of emptiness when being pressed lightly, a touch of insufficiency when being pressed strongly, and a touch of looseness a when the finger is lifted' (source: the Treasures of Eastern Medicine (東醫寶鑑)). In contrast, the forceful pulse is described as 'having strength while being pressed lightly or strongly and providing touches of hardness and substantiality', that is, 'as pulsating regularly and having strength' (source: the Treasures of Eastern Medicine (東醫寶鑑)).

Figure 13:
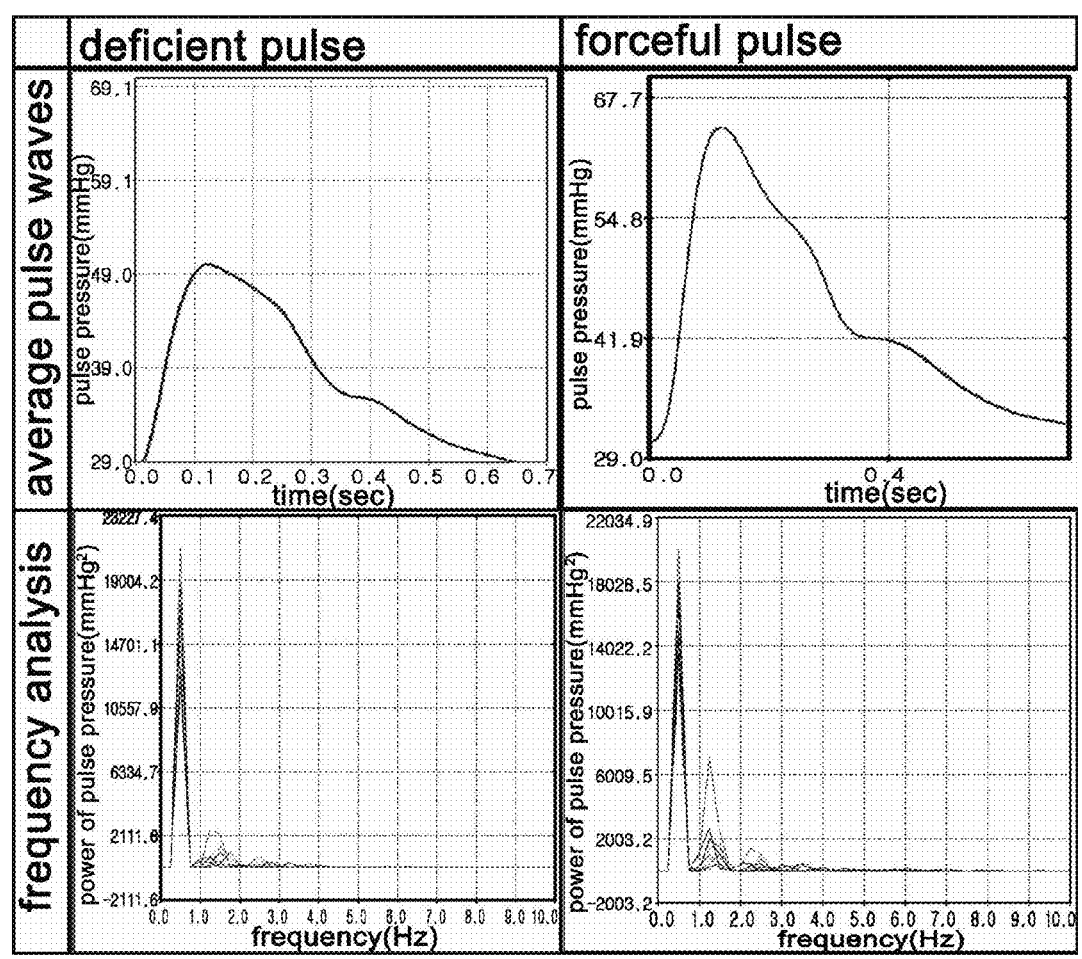
FIG. 13 is a diagram showing 'the representative pulse conditions of a deficient pulse and an forceful pulse which are drawed as average bits'.

FIG. 13 shows the representative conditions of a deficient pulse and an forceful pulse, obtained as average bits. More particularly, the average bits of a deficient pulse and an forceful pulse are constructed by averaging the pulse waves of 20 examinees whose pulses were diagnosed as either deficient pulses or forceful pulses by a traditional oriental doctor. The results of average bit analysis indicate that, in the case of a deficient pulse, the pulse pressure thereof is low and the wave width thereof is wide, while, in the case of an forceful pulse, the pulse pressure thereof is high and the wave width thereof is narrow.

Accordingly, when the definitions of a deficient pulse and an forceful pulse based on traditional oriental medicine are considered from the point of view of physics, the concepts of the deficient pulse and the forceful pulse may be defined as pulse conditions that are sensed depending on the intensity of pulse waves, therefore the present inventors designed output variables so that the deficient pulse and the forceful pulse could be distinguished from each other using indices related to the size and area of a wave cycle, such as maximum pulse pressure and wave width.

Measurement of Pulse Condition Information and Collection of Clinical Data

Collection of Clinical Data

Data was collected for 2459 persons who voluntarily applied for experiments in response to a public announcement about the experiments, and 689 healthy males and females who satisfied the requirements set forth in the following Table 3 were selected from the above persons.

TABLE 3

Requirements for selection of examinees for experiments
Requirements for selection person who does not have a disorder in the circulation of the blood
person who does not have a cardiac disorder, such as hypertension, hypotension, or arrhythmia
person whose pulse can be easily taken at the three Cun, Gu and Chi pulse-taking locations
person who had not had a meal within 30 minutes
person who had not had caffeine or smoked a cigarette within 30 minutes
person who had not drunk alcohol within 3 hours
for women, was not menstruating or pregnant The distribution of the ages of the 687 examinees who satisfied the above requirements is shown in the following Table 4.

TABLE 4

Number of examinees and distribution of ages

| Age | Male | Female | Total |
| --- | --- | --- | --- |
| teens | 66 | 36 | 102 |
| twenties | 45 | 43 | 88 |
| thirties~forties | 169 | 205 | 374 |
| 50 or above | 52 | 71 | 123 |
| total | 332 | 355 | 687 |

Measurement of Pulse Condition Information

The examinees' pulse condition information of Table 4 was measured through the follow process.

1. A traditional oriental doctor or a person who has pulse taking experience designates an examinee's Gu pulse taking location, and disposes a pulse-taking sensor at the Gu pulse taking location.

2. The range of pulse pressures, within which the examinee's pulsation can be detected at the Gu pulse taking location, is automatically detected by the sensor, the range is equally divided, and pulse condition information (pulse pressures), which is detected at respective pressing forces while the vertical transfer unit (or a robot hand) equipped with the pulse-taking sensor applies pressing forces, is measured and recorded.

More particularly, in a preferred embodiment of the present invention, pulse pressures are measured while pressing force is increased in steps from a first step to a fifth step.

The pressing force at the first step refers to pressing force at the time point at which a pulse pressure equal to or higher than a predetermined threshold value starts to be measured, and the pressing force at the fifth step refers to pressing force at the time point at which the pulse pressure is decreased to a value equal to or lower than the predetermined threshold value after being increased.

In a preferred embodiment of the present invention, it is preferred that the threshold value range from 1 to 5 mmHg. In particular, it is most preferable that the threshold value be 3 mmHg.

The range between the pressing force at the first step and the pressing force at the fifth step is defined as the pressing force range, the pressing force range is divided into equal intervals, and pulse pressures detected at respective pressing forces are measured.

3. The examinee's measured pulse pressures are received by the pulse-taking sensor, are passed through the A/D conversion unit for converting analog signal values into digital values, and are transferred to the deficient pulse and forceful pulse analytic apparatus connected to the pulse diagnostic device.

4. The data is sampled at predetermined regular intervals for a predetermined time period, the deficient pulse and forceful pulse analytic apparatus outputs the data, measured at respective steps, via a monitor or a printer and stores the data, and a deficiency/forceful coefficient is calculated and analyzed using the stored pulse diagnostic time-series data and an automatic analytic algorithm.

In a preferred embodiment of the present invention, in the case where the pressing range was divided into five equal steps and pressing was performed at respective steps, the most desirable data could be acquired when the sampling cycle was 256 Hz and the sampling time was 25 seconds.

Attempt at Quantifying Deficiency/Forceful Coefficient

The deficient pulse and forceful pulse determining device of the present invention was designed such that the deficiency/forceful coefficient was calculated using the following Equation 1 so as to implement the physical definitions of the deficient pulse and the forceful pulse, and the deficiency/forceful coefficient was quantified through the following process.

More particularly, clinical data, which was collected from 371 of the 687 examinees by traditional oriental doctors at the Gu pulse taking location for the diagnosis of deficient, intermediate, and forceful pulses, and traditional oriental doctors' pulse taking results are analyzed through comparison in light of statistics.

Comparison Between Persons Having Deficient Pulses and Persons Having Forceful Pulses Based on Traditional Oriental Doctors' Diagnosis for Normal Persons As the result of the diagnosis of deficient, intermediate and forceful pulses for 371 normal persons by traditional oriental doctors, analysis showed that 37 persons (9.97%) had deficient pulses, 301 persons (81.1%) had intermediate pulses, and 31 persons (8.89%) had forceful pulses.

Selection of Output Variables of Deficient Pulse and Forceful Pulse Diagnostic System Of the output variables of the pulse diagnostic system measured at the Gu pulse taking location on the basis of the deficient pulse and the forceful pulse diagnosed by traditional oriental doctors, variables, exhibiting significant average differences on the basis of a 5% significance level, were selected, as shown in the following Table 5.

TABLE 5

Output variables exhibiting significant average differences
based on results of diagnosis of traditional oriental doctors

| Name of variable | p-value |
| --- | --- |
| maximum pulse pressure during systole $h_P$ | 0.018 |
| maximum pulse pressure during diastole $h_D$ | 0.000 |

TABLE 5-continued

Output variables exhibiting significant average differences
based on results of diagnosis of traditional oriental doctors

| Name of variable | p-value |
|---|---|
| inflection point time between first peak and second peak during systole $t_Q$ | 0.021 |
| time period during systole $t_C$ | 0.011 |
| wave width $W_P$ | 0.000 |
| area during systole $A_S$ | 0.030 |
| area during diastole $A_D$ | 0.030 |
| wave angle $\Theta_P$ | 0.000 |

More particularly, of the variables extracted from the pulse pressure waveform, variables exhibiting significant differences through the results of the comparison with traditional oriental doctors' deficient pulse and forceful pulse diagnosis, are analyzed to include the 'maximum pulse pressure during systole $h_P$', the 'maximum pulse pressure during diastole $h_D$', the 'inflection point time between the first peak and the second peak during systole $t_Q$', the 'time period during systole $t_C$', 'wave width $W_P$', the 'area during systole $A_S$', the 'area during diastole $A_D$', and the 'wave angle $\Theta_P$'.

Analysis of Correlation Between Variables

The present inventors investigated the correlation between respective variables for the output variables of Table 5. The results are listed in the following Table 6.

In order to determine principal variables used by traditional oriental doctors so as to diagnose a deficient pulse and an forceful pulse, 8 variables, exhibiting significant differences between the results of the diagnosis of a deficient pulse and an forceful pulse by traditional oriental doctors and the output variables of the pulse diagnostic system, were selected as independent variables, that is, prediction variables. Additionally, correlation analysis was performed so as to determine the correlation between independent variables.

TABLE 6

Correlation between selected pulse diagnotic system output variables

| Correlation coefficient | Maximum pulse pressure | $h_D$ | $t_Q$ | $t_C$ | $W_P$ | $A_S$ | $A_D$ |
|---|---|---|---|---|---|---|---|
| $h_D$ | 0.47 | | | | | | |
| $t_Q$ | 0.36 | 0.36 | | | | | |
| $t_C$ | 0.28 | −0.11 | −0.06 | | | | |
| $W_P$ | −0.02 | −0.41 | −0.29 | 0.41 | | | |
| $A_S$ | 0.21 | −0.15 | −0.24 | 0.44 | 0.29 | | |
| $A_D$ | −0.21 | 0.15 | 0.24 | −0.44 | −0.29 | −1 | |
| $\Theta_P$ | −0.64 | −0.65 | −0.44 | 0.12 | 0.75 | 0.11 | −0.11 |

More particularly, in the case where a correlation coefficient has a value equal to or greater than 0.4, it is determined that there is a positive correlation between variables, and it is predicted that one variable will increase in proportion to the increase of another variable. In contrast, in the case where a correlation coefficient has a value equal to or less than −0.4, it is determined that there is a negative correlation between variables, and it is predicted that one variable decreases in proportion to the increase of another variable. However, when there is a high correlation between variables, it may be impossible to calculate a least squares estimator, and a problem may occur in that the variance of the estimator is increased. In this case, it is predicted that the problem of multicollinearity between variables, that is, the distortion of a portion, which can be explained by variables, versus a weight, may occur.

Multicollinearity occurs in the case where the correlation between variables is high or there is linear dependence between variables (refer to "Regression Analysis", authored by Keunsuk Gang and Chungrag Kim, and published in 1999 in Seoul by Gyou Pulishing Company, p. 147~148). In order to solve the problem of multicollinearity, it is preferred that one variable to be included in a regression model be selected from among the variables having the correlation, and thus the remaining variables be eliminated from the regression model.

Accordingly, variables are selected again, as shown in the following Table 7.

TABLE 7

Variables selected again so as to avoid multicollinearity problem

| Variable | Reselected variable | Reason |
|---|---|---|
| 1. maximum pulse pressure<br>2. $h_D$-$h_C$ | maximum pulse pressure | correlation coefficient 0.47 Influence of maximum pulse pressure is high |
| 1. wave width<br>2. $t_C$ | wave width | correlation coefficient 0.41 influence of wave width is high |
| 1. wave angle | eliminated | high correlation with maximum pulse pressure, $h_D$-$h_C$, $t_Q$ and wave width exists |
| 1. area during systole<br>2. area during diastole | area during systole | high correlation arbitrary selection of area during systole |

Logistic regression analysis is performed using the reselected variables of Table 7, that is, the 'maximum pulse pressure', the 'wave width', '$t_Q$' and the 'area during systole' so as to predict the deficient pulse and the forceful pulse.

More particularly, the logistic regression analysis is an analytic method that is used when predicting a dependent variable using an independent variable, which is a quantitative variable, in the case where the dependent variable is a qualitative variable having a bivariate value. Linear regression analysis minimizes the sum of squared residuals, while logistic regression analysis predicts the coefficient of regression while likelihood, that is, the possibility of occurrence of an event, increases. The program used was SPSS 12.0 (vendor: "Data Solution Inc."), and forward stepwise regression was selected as a criterion for the selection of independent variable input.

Figure 15:
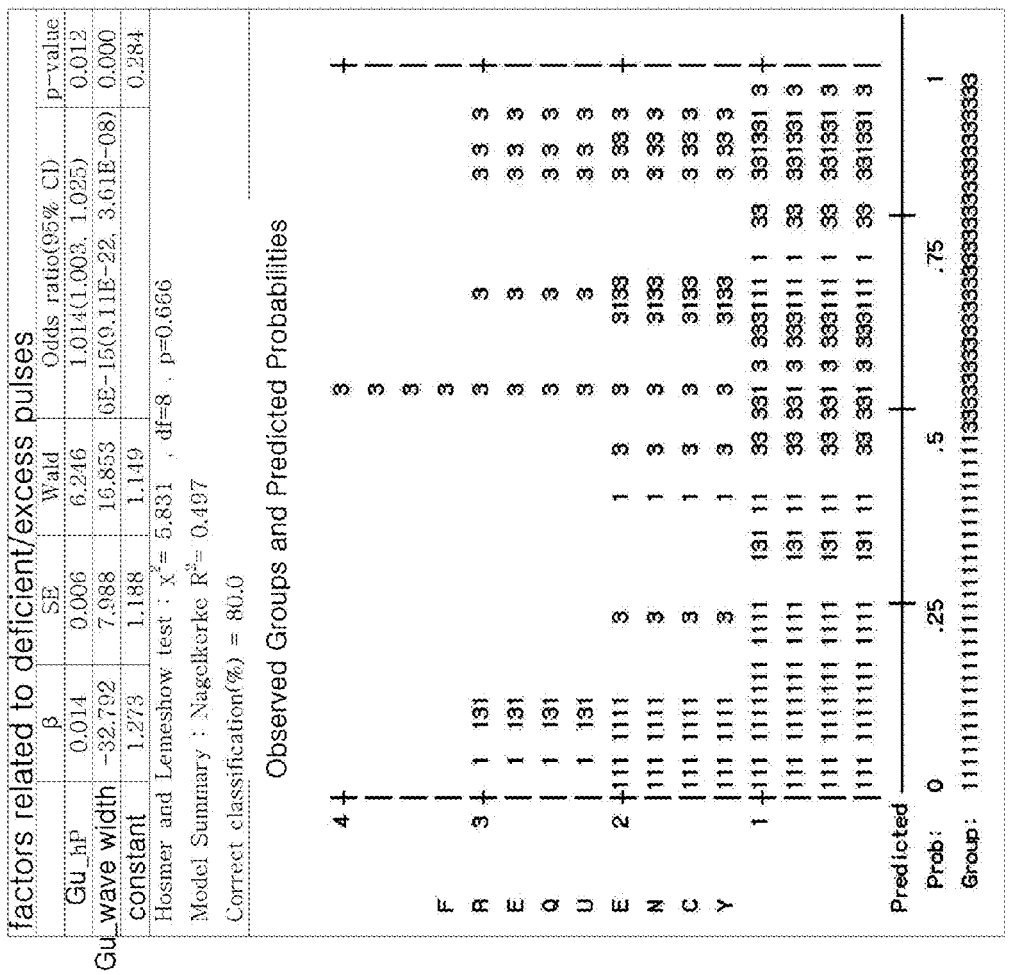
FIG. 15 is a table showing 'results of logistic regression analysis that is performed using maximum pulse pressure during systole ($h_P$) and wave width ($W_P$) as independent variables'.

FIG. 15 shows the results of a process of performing logistic regression analysis using the maximum pulse pressure, the wave width, $t_Q$ and the area during systole, selected again from among the eight variables exhibiting significant differences between the deficient pulse and the forceful pulse as the result of pulse taking by the traditional oriental doctors so as to avoid multicollinearity, as independent variables, that is, prediction variables, and selecting variables that were good predictors.

In the logistic regression model presented in FIG. 15, the optimal discriminant is expressed as Equation 1.

More particularly, as the result of Hosmer-Lemeshow statistical analysis, the Chi-square value was found to be 5.831, thus showing that the fit of the model was desirable, the explanatory power of the regression model for the dependent variable was 49.7%, and the accuracy of the formed model for the deficient and forceful pulses was 80%.

Of the 'maximum pulse pressure', the 'wave width', $t_Q$ and the 'area during systole', $t_Q$ and the 'area during systole' were eliminated so as to maximize the compatibility of the prediction of the model. As a result, it was found that the two variables included in the regression model, that is, 'maximum pulse pressure' and 'wave width', were both significant variables, and, whenever the maximum pulse pressure increased by 1, the probability of a pulse being an forceful pulse increased 1.014 times as much as the probability of being a deficient pulse.

Figure 16:
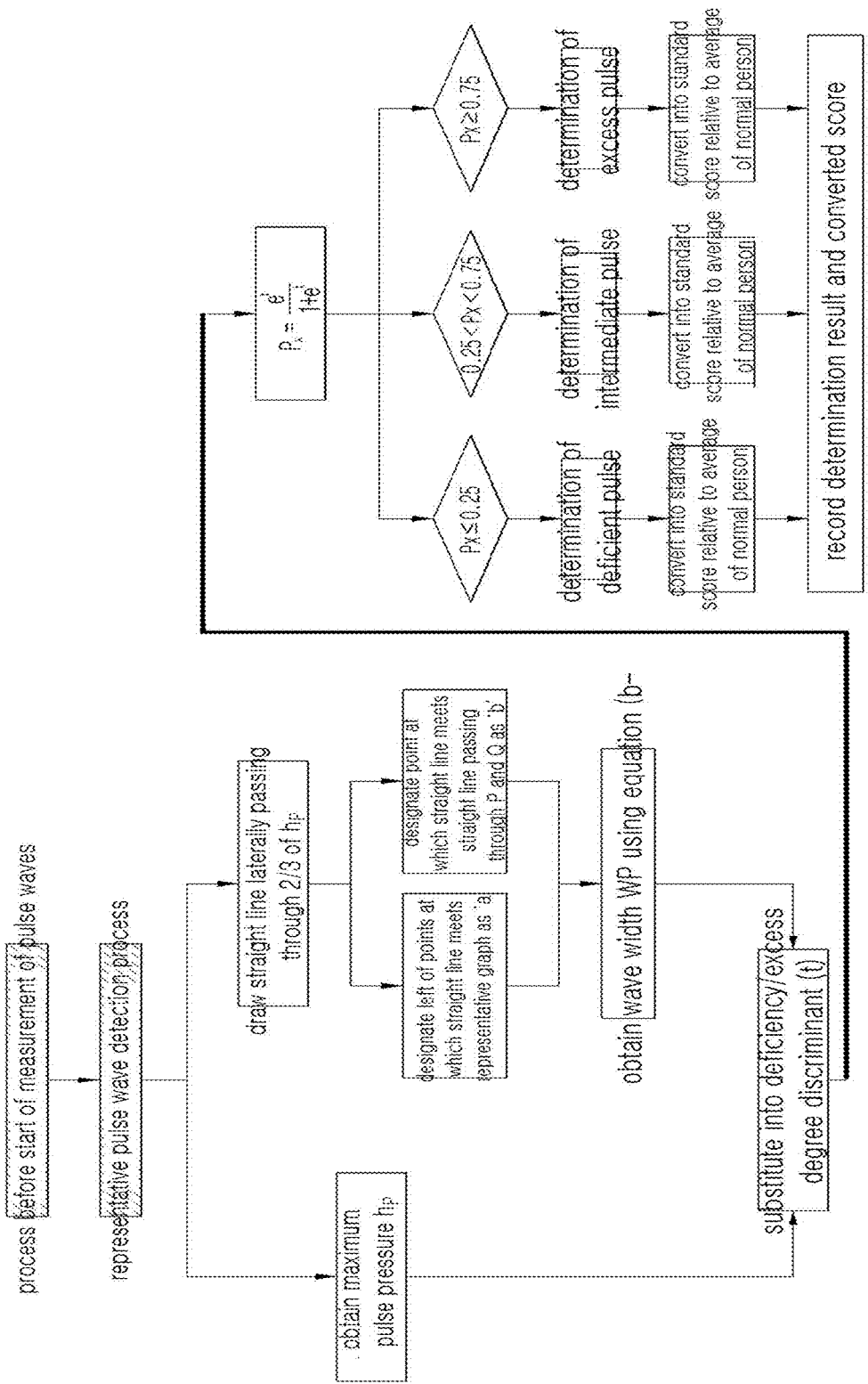
FIG. 16 is a flowchart showing 'the flow of the deficient pulse and forceful pulse condition analysis' of the deficient pulse and forceful pulse diagnotic system according to the present invention.

On the basis of the results of the analysis, the flow of the pulse diagnostic analysis of the deficient pulse and forceful pulse diagnostic system according to the present invention, in which the optimal discriminant is calculated, will be described in detail based on the 'flowchart of the deficient pulse and forceful pulse condition analysis', which is shown in FIG. 16.

1. A traditional oriental doctor or a person who has pulse taking experience designates an examinee's Gu pulse taking location, and disposes the pulse-taking sensor at the Gu pulse taking location. This process is illustrated as a 'process before the start of the measurement of pulse waves' in the flowchart of FIG. 16.

2. The range of pulse pressures, within which the examinee's pulsation can be detected at the Gu pulse taking location, is automatically detected by the sensor, the range is equally divided, and pulse pressure information (variation in pulse pressure over the time of the measurement of pulse pressure, that is, a pulse waveform), which is detected at respective pressing forces while a robot hand, equipped with the pulse-taking sensor, applies pressing force, is measured and recorded.

In a preferred embodiment of the present invention, it is preferred that a multichannel array sensor in which five sensors are disposed in a cross arrangement be used as the sensor. It is preferred that the pressing step include 5 steps.

3. The examinee's pulse pressure information is received by the pulse-taking sensor, is passed through the A/D conversion unit for converting analog signal values into digital values, and is transmitted to the deficient pulse and forceful pulse analytic apparatus connected to the pulse diagnostic device. The processes 2 and 3 are illustrated as a 'representative pulse wavebit detection process' in the flowchart of FIG. 16.

4. The transmitted data is sampled at predetermined regular intervals for a predetermined time period, the deficient pulse and forceful pulse analytic apparatus outputs the data, measured at respective steps, via a monitor or a printer and stores the data, and a deficiency/forceful coefficient is calculated and analyzed using the stored pulse diagnostic time-series data and an analytic algorithm.

More particularly, the deficient pulse and forceful pulse determining device measures pulse waves (a pulse pressure waveform) in the pressing step, in which the pulse pressure, which is measured while the pressing force increases in steps, becomes maximal. Thereafter, an average bit is created through an ensemble averaging process of searching each of a plurality of pulse wave bits for a start point, a peak point and an end point, separating them for each bit, overlapping the bits on the basis of peak points, and obtaining the average value of pulse pressure values (along the y axis) occurring at the same time point (along the x axis), and the average bit is determined to be a representative bit.

The maximum pulse pressure value $h_P$ and the wave width $W_P$ along the pulse pressure axis, which correspond to the created representative bit during systole, are detected. The 'wave width $W_P$' is defined as the difference 'b−a' when the x-axis coordinate value of the left of the points, at which a straight line laterally extending through the pulse pressure values that correspond to ⅔ of the representative pulse pressure $h_P$ meets a representative bit curve, is designated as 'a' and the x-axis coordinate value of the point at which the straight line meets a straight line passing through a point P and a point Q is designated as 'b'.

The primitive value of the deficiency/forceful coefficient is calculated using respective detected variables and Equation 1. The determination means of the present invention calculates the value of the deficiency/forceful coefficient Px using Equation 2, and determines the pulse of interest to be a deficient pulse when the calculated Px value falls within a range from 0 to 0.25, and to be an forceful pulse when a pulse of interest falls within a range from 0.75 to 1.0.

In a preferred embodiment of the present invention, a deficient pulse and forceful pulse diagnostic system is designed such that conversion means for converting a primitive value into a standard score based on a massive clinical DB using the deficiency/forceful coefficient, obtained through the calculation using Equation 1, as the primitive value, is added to the deficient pulse and forceful pulse diagnostic system to which the quantified deficiency/forceful coefficient is applied, thereby being capable of evaluating an examinee's relative position (refer to FIG. 17).

Significance Test

In order to test the significance of the deficient pulse and forceful pulse diagnostic system of the present invention, in which quantified output variables are calculated, the results of the traditional oriental doctors' pulse taking were compared with the results of the diagnostic system of the present invention.

Figure 18:
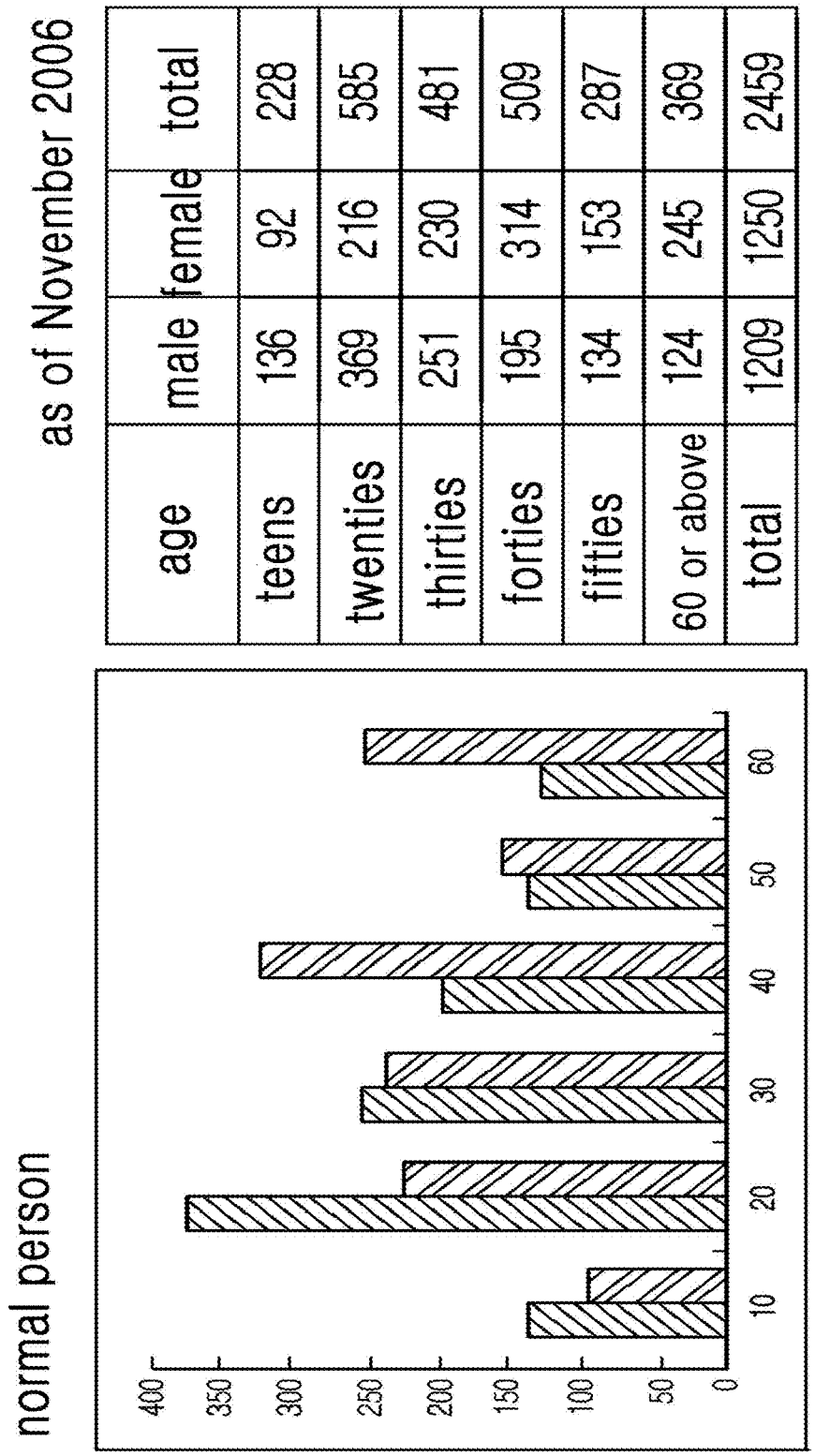
FIG. 18 is a diagram showing the status of the collection of clinical data using the deficient pulse and forceful pulse diagnotic system according to the present invention as of November 2006.

More particularly, a massive clinical DB was constructed by collecting the results of diagnosis of the traditional oriental doctors as well as the results of the deficient pulse and forceful pulse analysis of the pulse diagnostic system, which was designed based on the deficiency/forceful coefficient quantified for a total of 2459 persons (as of November 2006), including the examinees for the collection of clinical data (refer to FIG. 18).

Figure 19:
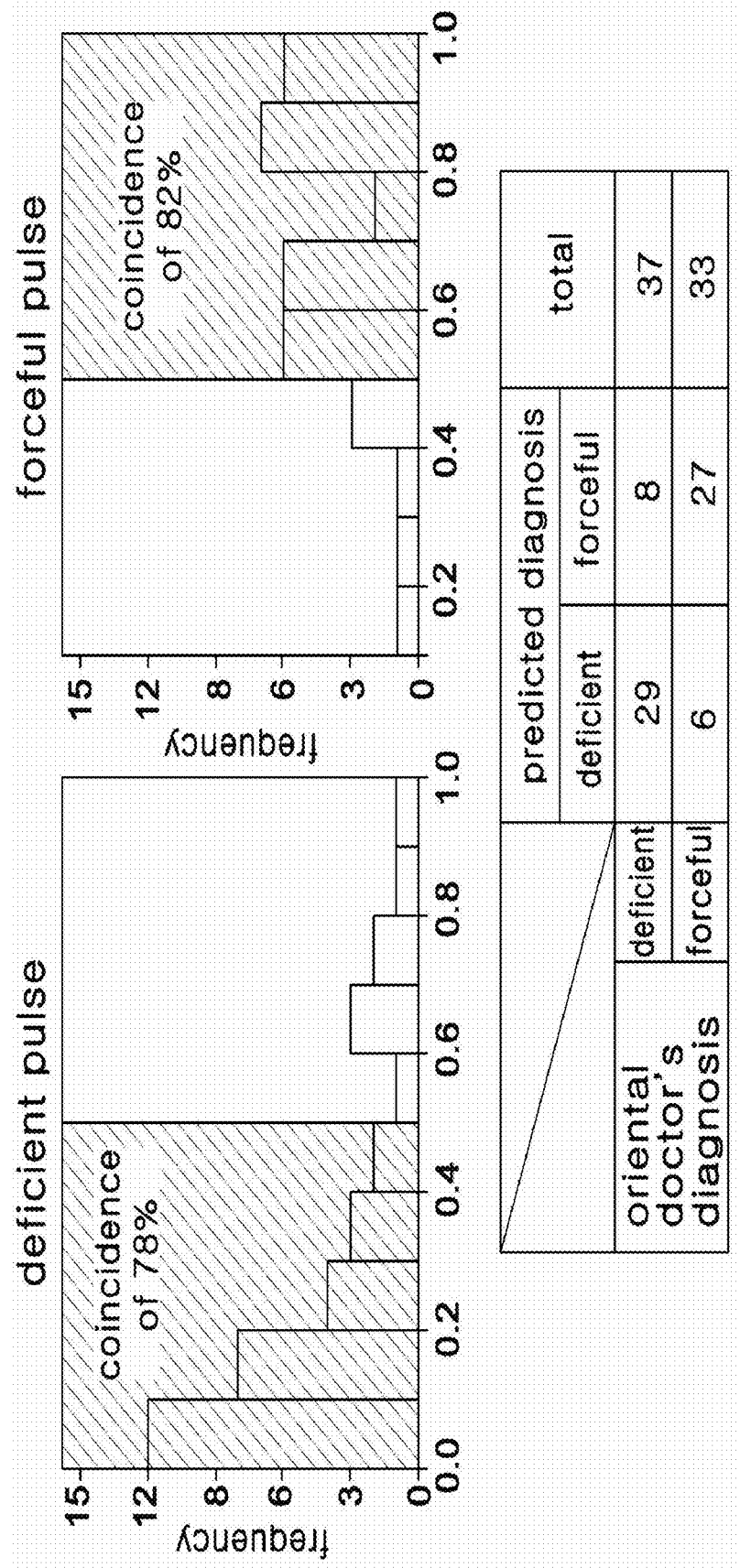
FIG. 19 is a diagram showing 'results of traditional oriental doctors' pulse taking and results of the significance analysis of the deficient pulse and forceful pulse diagnotic system'.

687 persons satisfying the selection requirements set forth in Table 3 were selected from the constructed massive clinical DB as a sample, and a significance analysis was performed between the results of the diagnosis of the traditional oriental doctors and the performance of the deficient pulse and forceful pulse diagnostic system (refer to FIG. 19).

More particularly, when diagnosis was performed on 371 persons (37 persons having deficient pulses, 301 persons having intermediate pulses, and 33 persons having forceful pulses), whose pulses were diagnosed by the traditional oriental doctors, using the pulse diagnostic system according to the present invention, analysis showed that 29 persons had deficient pulses and 27 persons had forceful pulses.

When the results of the diagnosis of the traditional oriental doctors were compared with the results of the diagnosis of the pulse diagnostic system, analysis showed that the degree of coincidence was 78% for the deficient pulse and the degree of coincidence was 82% for the forceful pulse, which shows that there is a high correlation between the results of the pulse taking of the traditional oriental doctors and the results of the diagnosis of the deficient pulse and forceful pulse diagnostic system according to the present invention.

Meanwhile, since the results of traditional oriental doctors' pulse taking vary with the examiners' emotional conditions, physical conditions, and skill levels, the deficient pulse and forceful pulse diagnostic system according to the present invention provides results of pulse condition diagnosis that are faithful to original oriental medicine texts, are more objective, and have high reproducibility and reliability.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A system for diagnosing a deficient pulse and a forceful pulse, comprising:

a pulse diagnostic device for measuring pulse condition information at an examinee's Cun (寸), Gu (關), and Chi (尺) pulse-taking locations on his or her wrist using one or more pulse-taking sensors;

a deficient pulse and forceful pulse determining device operably connected to the pulse diagnostic device, and configured to analyze the pulse pressure information measured by the pulse diagnostic device, to calculate a quantified deficiency/forceful coefficient and to determine whether a pulse of interest is a deficient pulse or an forceful pulse and an output device connected to the determining device and configured to display results of the determination, wherein the deficient pulse and forceful pulse determining device includes storage means for receiving and storing pulse pressure information, measured by the pressure sensor of the pulse diagnostic device, which comes into contact with a pulse taking location;

graphing means for receiving the stored pulse pressure information and converting variation in pulse pressure over time into a graph;

selection means for selecting 'maximum pulse pressure during systole $h_P$', 'maximum pulse pressure during diastole $h_D$', 'inflection point time period between a first peak and a second peak during systole $t_Q$', 'systole time $t_C$', 'wave width $W_P$', 'systole area $A_S$' and 'diastole area $A_D$', and 'wave angle $\theta_P$' from the graph as calculation variables;

deficiency/forceful coefficient calculation means for calculating a deficiency/forceful coefficient using the selected calculation variables;

deficient and forceful pulse determination means for determining whether an examinee's pulse is a deficient pulse or an forceful pulse based on the calculated deficiency/forceful coefficient; and transmission means for transmitting results of the deficient and forceful pulse determination to the output device, wherein the 'maximum pulse pressure during systole $h_P$' is defined as a pulse pressure-axis maximum value of a first peak during systole, the 'maximum pulse pressure during diastole $h_D$' is defined as a pulse pressure-axis maximum value of a peak during diastole, the 'inflection point time period between a first peak and a second peak during systole $t_Q$' is defined as a difference between a time-axis value of an inflection point Q between the first peak and the second peak during systole and a time-axis value of a point S at which the first peak during systole is created, the 'systole time $t_C$' is defined as a difference between a time-axis value of an inflection point C between the second peak during systole and the peak during diastole and a time-axis value of a point S at which a pulse pressure wave form during systole starts, the 'wave width $W_P$' is defined as a difference 'b-a', when the x-axis coordinate value of a leftmost point among the points at which a straight line extending through the pulse pressure values that correspond to ⅔ of the representative pulse $h_P$ meets the first peak during systole is designated as 'a', and the x-axis coordinate value of the point at which the straight line meets a straight line passing through the inflection point Q between the first peak and the second peak during systole and through a highest point P of the first peak during systole is designated as 'b', the 'systole area $A_S$' is defined as a value obtained by integrating pressures over a time period from the start point S of the pulse pressure wave form during systole to the inflection point C between the second peak during systole and the peak during diastole, the 'diastole area $A_D$' is defined as a value obtained by integrating pressures over the time period from the point C to the point S in a next cycle, and the 'ave angle $\theta_P$' is defined as an angle included between a straight line connecting the highest point P of the first peak during a systole with 'a' and a straight line connecting the highest point P of the first peak during systole with 'b'.

2. The system as set forth in claim 1, wherein the pulse diagnostic device comprises a wrist holding unit for securing an examinee's wrist, the pulse-taking sensors for coming into contact with an inner surface of the examinee's wrist, measuring pulse pressure at three Cun, Gu and Chi pulse-taking locations, and outputting corresponding electrical signals, a lateral transfer unit for enabling lateral transfer of the pulse-taking sensors, a vertical transfer unit for adjusting pressures applied by the pulse-taking sensors to the examinee's pulse taking portions, in steps, a microprocessor for controlling lateral and vertical locations of the pulse-taking sensors, an amplifier for amplifying analog signals from the pulse-taking sensors, a filter unit for filtering out noise from the amplified analog signals, an A/D conversion unit for converting the filtered, amplified analog signals into digital signals, and a communication interface for communicating with the deficient pulse and forceful pulse determining device.

3. The system as set forth in claim 1, wherein the one or more pulse-taking sensors are composed of pressure sensors, including pressure detection elements, or an array sensor, including semiconductor pressure sensors.

4. The system as set forth in claim 3, wherein the array sensor has an arrangement in which 5 to 13 semiconductor pressure sensors are disposed in one arrangement selected from the group consisting of a cross, square, rectangular, diamond and hexagonal arrangements.

5. The system as set forth in claim 4, wherein the array sensor is configured such that 5 semiconductor pressure sensors are disposed in a cross arrangement.

6. The system as set forth in claim 1, wherein the pressure applied to the pulse taking locations is adjusted in 3 to 10 steps.

7. The system as set forth in claim 6, wherein the pressure applied to the pulse taking locations is adjusted in 5 steps.

8. The system as set forth in claim 1, wherein the deficiency/forceful coefficient is calculated using a discriminant expressed in the following Equation 1:

$$t=1.273+0.014 \times h_P - 32.792 \times W_P$$

where t is the deficiency/forceful coefficient, $h_P$ is maximum pulse pressure during systole, and $W_P$ is wave width.

9. The system as set forth in claim 1, wherein the deficient pulse and forceful pulse determining device calculates a Px value using the following Equation 2, and determines a pulse of interest to be a deficient pulse if the calculated Px value satisfies $0 \leq Px \leq 0.25$, to be intermediate pulse if the value satisfies $0.25 < Px < 0.75$, and to be forceful pulse if the calculated Px value satisfies $0.75 \leq Px \leq 1.0$:

$$P_x = \frac{e^t}{1+e^t}$$

where t is a primitive value of the deficiency/forceful coefficient calculated using Equation 1: $t=1.273+0.014 \times h_p - 32.792 \times W_p$ where t is the deficiency/forceful coefficient, $h_p$ is the maximum pulse pressure during systole, and $W_p$ is wave width.

10. The system as set forth in claim 1, wherein the deficient pulse and forceful pulse determining device further comprises conversion means for converting a value of the deficiency/forceful coefficient value into a standard score calculated based on a clinical database.

11. The system as set forth in claim 10, wherein the conversion means comprises:
    a storage module for receiving and storing pulse diagnostic information collected from a population of normal persons;
    a calculation module for calculating the deficiency/forceful coefficient using the stored pulse diagnostic information;
    an arrangement module for arranging calculated deficiency/forceful coefficients in descending order;
    a distribution chart preparation module for preparing a distribution chart for the arranged deficiency/forceful coefficients; and
    a quartile calculation module for calculating quartiles, indicating the relative positions occupied by the respective calculated deficiency/forceful coefficients, from the prepared distribution chart and converting the quartiles into standard scores.

12. The system as set forth in claim 11, wherein the arrangement module arranges the deficiency/forceful coefficients according to age or gender.

13. The system as set forth in claim 1, wherein the deficient pulse and forceful pulse determining device further Comprises an auxiliary storage device for storing results of the determination of a deficient pulse or an forceful pulse in a file form.

14. The system as set forth in claim 1, wherein the deficient pulse and forceful pulse determining device further comprises an input device for inputting the examinee's information.

* * * * *